United States Patent
Smith Resar et al.

(10) Patent No.: US 10,213,454 B2
(45) Date of Patent: Feb. 26, 2019

(54) METHODS OF INHIBITING CANCER STEM CELLS WITH HMGA1 INHIBITORS

(71) Applicant: THE JOHNS HOPKINS UNIVERSITY, Baltimore, MD (US)

(72) Inventors: Linda M. Smith Resar, Stevenson, MD (US); David Huso, Parkton, MD (US); Leslie Cope, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 0 days.

(21) Appl. No.: 15/398,944

(22) Filed: Jan. 5, 2017

(65) Prior Publication Data

US 2017/0202867 A1     Jul. 20, 2017

Related U.S. Application Data

(62) Division of application No. 14/701,586, filed on May 1, 2015, now Pat. No. 9,545,417.

(60) Provisional application No. 61/987,264, filed on May 1, 2014.

(51) Int. Cl.

| | |
|---|---|
| *A61K 48/00* | (2006.01) |
| *C07H 21/02* | (2006.01) |
| *A61K 31/713* | (2006.01) |
| *G01N 33/574* | (2006.01) |
| *A61K 31/7068* | (2006.01) |
| *C12Q 1/68* | (2018.01) |
| *C12N 15/113* | (2010.01) |
| *C12Q 1/6886* | (2018.01) |
| *A61K 9/14* | (2006.01) |
| *A61K 45/06* | (2006.01) |
| *A61K 31/7105* | (2006.01) |

(52) U.S. Cl.
CPC .............. *A61K 31/713* (2013.01); *A61K 9/14* (2013.01); *A61K 31/7068* (2013.01); *A61K 31/7105* (2013.01); *A61K 45/06* (2013.01); *C12N 15/113* (2013.01); *C12Q 1/68* (2013.01); *C12Q 1/6886* (2013.01); *G01N 33/5748* (2013.01); *G01N 33/57407* (2013.01); *G01N 33/57484* (2013.01); *C12N 2310/14* (2013.01); *C12N 2310/531* (2013.01); *C12N 2320/30* (2013.01); *C12Q 2600/106* (2013.01); *C12Q 2600/158* (2013.01); *C12Q 2600/178* (2013.01)

(58) Field of Classification Search
CPC . A61K 31/713; C12N 2310/11; C12N 15/113
See application file for complete search history.

(56) References Cited

U.S. PATENT DOCUMENTS

| | | |
|---|---|---|
| 6,506,559 B1 | 1/2003 | Fire et al. |
| 6,573,099 B2 | 6/2003 | Graham |
| 2003/0153519 A1 | 8/2003 | Kay et al. |
| 2003/0167490 A1 | 9/2003 | Hunter et al. |
| 2012/0108656 A1 | 5/2012 | Zollo |
| 2013/0266639 A1 | 10/2013 | Rao |
| 2014/0087400 A1 | 3/2014 | Alper |
| 2016/0136195 A1* | 5/2016 | Kennedy .............. C12N 15/113 |

FOREIGN PATENT DOCUMENTS

| | | |
|---|---|---|
| WO | 2013/075059 A1 | 5/2013 |
| WO | 2013075059 A1 | 5/2013 |

OTHER PUBLICATIONS

Williams MD et al., HMGA1 drives metabolomics reprogramming of intestinal epithelium during hyperproliferation, polyposis and colorectal carcinogenesis. J Proteome Res 2015;14:1420-31.
All AH et al., Early intervention for spinal cord injury with human induced pluripotent stem cells oligodendrocyte progenitors PLoS ONE 2015; 10:e0116933.
Nilliams MD et al., Characterizing metabolic changes in human colorectal cancer. Analytical Bioanalytical Chem 2015.
Monroe A et al., Through a gender lens: A view of gender and leadership positions in a Department of Medicine at one academic health center. Journal of Women's Health 2015.
Resar LMS & Frank S. What to do when you can't transfuse. Hematology 2014;2014:553-8.
Xian L et al., IBRUTinib: BRUTe Force against Bortezomib-Resistant Myeloma Cells. Cell Cycle, 2015.
Anele UA et al., How I treat priapism. Blood, Jun. 4, 2015; 3551-3558.
Barrett et al., NCBI GEO: mining millions of expression profiles—database and tools, (2005) Nucleic Acids Res. 33: D562-D566.
Belton et al., HMGA1 Induces Intestinal Polyposis in Transgenic Mice and Drives Tumor Progression and Stem Cell Properties in Colon Cancer Cells, (2012) PloS One 7:e30034.
Ben-Porath et al., An embryonic stem cell-like gene expression signature in poorly differentiated aggressive human tumors, (2008) Nat. Genet. 40:499-507.
Bock et al., Reference Maps of Human ES and iPS Cell Variation Enable High-Throughput Characterization of Pluripotent Cell Lines, (2011) Cell 44: 439-452.
Carey et al., The Triple Negative Paradox: Primary Tumor Chemosensitivity of Breast Cancer Subtypes, (2007) Clin. Cancer Res. 13:2329-2334.
Carvalho et al., A framework for oligonucleotide microarray pre-processing, (2010) Bioinformatics 26: 2363-2367.
Chou et al., Efficient human iPS cell derivation by a non-integrating plasmid from blood cells with unique epigenetic and gene expression signatures, (2011) Cell Res. 21:518-529.

(Continued)

Primary Examiner — Amy H Bowman
(74) Attorney, Agent, or Firm — Johns Hopkins Technology Ventures

(57) ABSTRACT

The presently disclosed subject matter relates to methods of inhibiting cancer stem cells and growth of aggressive and/or poorly differentiated metastatic tumors comprising the cancer stem cells with HMGA1 inhibitors. The presently disclosed subject matter also provides methods of selecting and treating a subject with aggressive and/or poorly differentiated metastatic cancer using HMGA1 inhibitors.

15 Claims, 19 Drawing Sheets

Specification includes a Sequence Listing.

(56) References Cited

OTHER PUBLICATIONS

Coburn et al., Potent and Specific Inhibition of Human Immunodeficiency Virus Type 1 Replication by RNA Interference. (2002) J. Virol. 76:9225.
Dang, Cancer Cell Metabolism: There is No ROS for the Weary, (2012) Cell 2:304-307.
Dent et al., Triple-Negative Breast Cancer: Clinical Features and Patterns of Recurrence, (2007) Clin. Cancer Res. 13:4429-4434.
Dhar et al., Dominant-negative c-Jun (TAM67) target genes: HMGA1 is required for tumor promoter-induced transformation, (2004) Oncogene 23:4466-4476.
Di Cello et al., Inactivation of the Cdkn2a locus cooperates with HMGA1 to drive T-cell leukemogenesis, (2013) Leuk. Lymphoma 54:1762-1768.
Di Cello et al., Cyclooxygenase inhibitors block uterine tumorigenesis in HMGA1a transgenic mice and human xenografts, (2008) Molecular Cancer Therapuetics 7:2090-2095.
Flohr et al., High mobility group protein HMGA1 expression in breast cancer reveals a positive correlation with tumour grade, (2003) Histol. Histopathol. 18: 999-1004.
Fusco et al., Roles of HMGA proteins in cancer, (2007) Nat. Rev. Cancer 7:899-910.
Gentleman et al., Bioconductor: open software development for computational biology and bioinformatics, (2004) Genome Biol. 5: R80.
Haffty,Locoregional Relapse and Distant Metastasis in Conservatively Managed Triple Negative Early-Stage Breast Cancer, (2006) J. Clin. Oncol. 24:5652-5657.
Hillion et al., The High-Mobility Group A1a/Signal Transducer and Activator of Transcription-3 Axis: An Achilles Heel for Hematopoietic Malignancies?, (2008) Cancer Res. 68:10121-10127.
Hillion et al., Up-regulation of MMP-2 by HMGA1 Promotes Transformation in Undifferentiated, Large Cell Lung Cancer, (2009) Mol. Cancer Res. 7:1803-1812.
Hommura et al., HMG-I/Y is a c-Jun/Activator Protein-1 Target Gene and is Necessary for c-Jun-Induced Anchorage-Independent Growth in Rat1a Cells, (2004) Mol. Cancer Res. 2:305-314.
Hristov et al., HMGA1 correlates with advanced tumor grade and decreased survival in pancreatic ductal adenocarcinoma, (2010) Mod. Pathol. 23: 98-104.
Irizarry et al., Summaries of Affymetrix GeneChip probe level data, (2003) Nucleic Acids Res. 31: e15.
Karp et al., Phase 1 and pharmacokinetic study of bolus-infusion flavopiridol followed by cytosine arabinoside and mitoxantrone for acute leukemias, (2011) Blood 117:3302-3310.
Lee et al., Basal-like breast cancer displays distinct patterns of promoter methylation, (2010) Cancer Biol. Ther. 9:1017-1024.
Mani et al., The Epithelial-Mesenchymal Transition Generates Cells with Properties of Stem Cells, (2008) Cell 133:704-715.
Massague, TGFβ in Cancer, (2008) Cell 134: 215-230.
Muromoto et al., BART is essential for nuclear retention of STAT3, (2008) Int. Immunol. 20: 395-403.
Nelson et al., Flavopiridol induces BCL-2 expression and represses oncogenic transcription factors in leukemic blasts from adults with refractory acute myeloid leukemia, (2011) Leuk Lymphoma 52:1999-2006.
Nie et al., c-Myc Is a Universal Amplifier of Expressed Genes in Lymphocytes and Embryonic Stem Cells, (2012) Cell 151:68-79.
Pedulla et al., Sequence and analysis of the murine Hmgiy (Hmga1) gene locus, (2001) Gene 271:51-58.
Pegram et al., Phase II Study of Receptor-Enhanced Chemosensitivity Using Recombinant Humanized Anti-p185HER2/neu Monoclonal Antibody Plus Cisplatin in Patients With HER2/neu-Overexpressing Metastatic Breast Cancer Refractory to Chemotherapy Treatment, (1998) J. Clin. Oncol. 16:2659-2671.
Pomeroy et al., Prediction of central nervous system embryonal tumour outcome based on gene expression, (2002) Nature 415: 436-442.
Reeves et al., Architectural Transcription Factor HMGI(Y) Promotes Tumor Progression and Mesenchymal Transition of Human Epithelial Cells, (2001) Mol. Cell. Biol. 21:575-594.
Reeves et al., HMGI/Y proteins: £exible regulators of transcription and chromatin structure, (2001) Biochim. Biophys. Acta 1519:13-29.
Reeves, HMG Nuclear Proteins: Linking Chromatin Structure to Cellular Phenotype, (2010) Biochim. Biophys. Acta 1799:3-14.
Resar, The High Mobility Group A1 Gene: Transforming Inflammatory Signals into Cancer?, (2010) Cancer Research 10:436-439.
Schuldenfrei et al., HMGA1 drives stem cell, inflammatory pathway, and cell cycle progression genes during lymphoid tumorigenesis, (2011) BMC Genomics 12:549.
Semenza, Cancer-stromal cell interactions mediated by hypoxia-inducible factors promote angiogenesis, lymphangiogenesis, and metastasis, (2012) Oncogene, 32, 4057-4063.
Shah et al., High mobility group A1 and cancer: Potential biomarker and therapeutic target, (2012) Histol. Histopathol. 27:567-579.
Shah et al., HMGA1 Reprograms Somatic Cells into Pluripotent Stem Cells by Inducing Stem Cell Transcriptional Networks, (2012) PLoS One 7: e48533.
Shaw et al., A Detailed Mammosphere Assay Protocol for the Quantification of Breast Stem Cell Activity, (2012) J. Mammary Gland Biol. Neoplasia 17: 111-117.
Siegel et al., Cancer Statistics, 2013, (2013) CA Cancer J. Clin. 63:11-30.
Smyth, 23 Limma: Linear Models for Microarray Data, Bioinformatics and Computational Biology Solutions using R and Bioconductor, (2015) Springer-Verlag: 397-420.
Stewart et al., Lentivirus-delivered stable gene silencing by RNAi in primary cells, (2003) RNA 9:493-501.
Takaha et al., HighMobilityGroup ProteinHMGI(Y) Enhances TumorCellGrowth, Invasion, and Matrix Metalloproteinase-2 Expression in ProstateCancerCells, (2004) The Prostate 60:160-167.
Tesfaye et al., The High-Mobility Group A1 Gene Up-Regulates Cyclooxygenase 2 Expression in Uterine Tumorigenesis, (2007) Cancer Res. 67:3998-4004.
Thibodeaux et al., Immortalization and transformation of human mammary epithelial cells by a tumor-derived Myc mutant, (2009) Breast Cancer Res. Treat. 116:281-294.
Tront et al., Gadd45a Functions as a Promoter or Suppressor of Breast Cancer Dependent on the Oncogenic Stress, (2010) Cancer Res. 70:9671-9681.
Wiggans et al., Phase-II Trial of Tamoxifen in Advanced Breast Cancer, (1979) Cancer Chemother. Pharmacol. 3:45-48.
Williams et al., Metabolomics of colorectal cancer: past and current analytical platforms, (2013) Anal. Bioanal. Chem. 405:5013-5030.
Wood et al., HMG-I/Y, a New c-Myc Target Gene and Potential Oncogene, (2000) Mol. Cell. Biol. 20:5490-5502.
Xu et al., The HMG-I Oncogene Causes Highly Penetrant, Aggressive Lymphoid Malignancy in Transgenic Mice and Is Overexpressed in Human Leukemia, (2004) Cancer Res. 64:3371-3375.
Zhou et al., The pattern of gene expression in human CD34+ stem/progenitor cells, (2001) Proc. Natl. Acad. Sci. USA 98:13966-13971.
Dolde et al., HMG-I/Y in human breast cancer cell lines. (2002) Breast Cancer Research and Treatment 71: 181-191.
Scherr, et al., "Modulation of gene expression by lentiviral-mediated delivery of small interfering RNA", Cell Cycle (2003) vol. 2, No. 3, pp. 251-257.
Huso et al (2014) The high mobility group A1 molecular switch: turning on cancer—can we turn it off? Expert Opin Ther Targets. May 2014;18(5):541-53. doi: 10.1517/14728222.2014.900045. Epub Mar. 31, 2014.
Shah et al (2013) HMGA1: a master regulator of tumor progression in triple-negative breast cancer cells. PLoS One. May 2, 2013;8(5):e63419. doi: 10.1371/journal.pone.0063419. Print 2013.
Liau et al (2006) HMGA1 is a determinant of cellular invasiveness and in vivo metastatic potential in pancreatic adenocarcinoma. Cancer Res. Dec. 15, 2006;66(24):11613-22.

\* cited by examiner

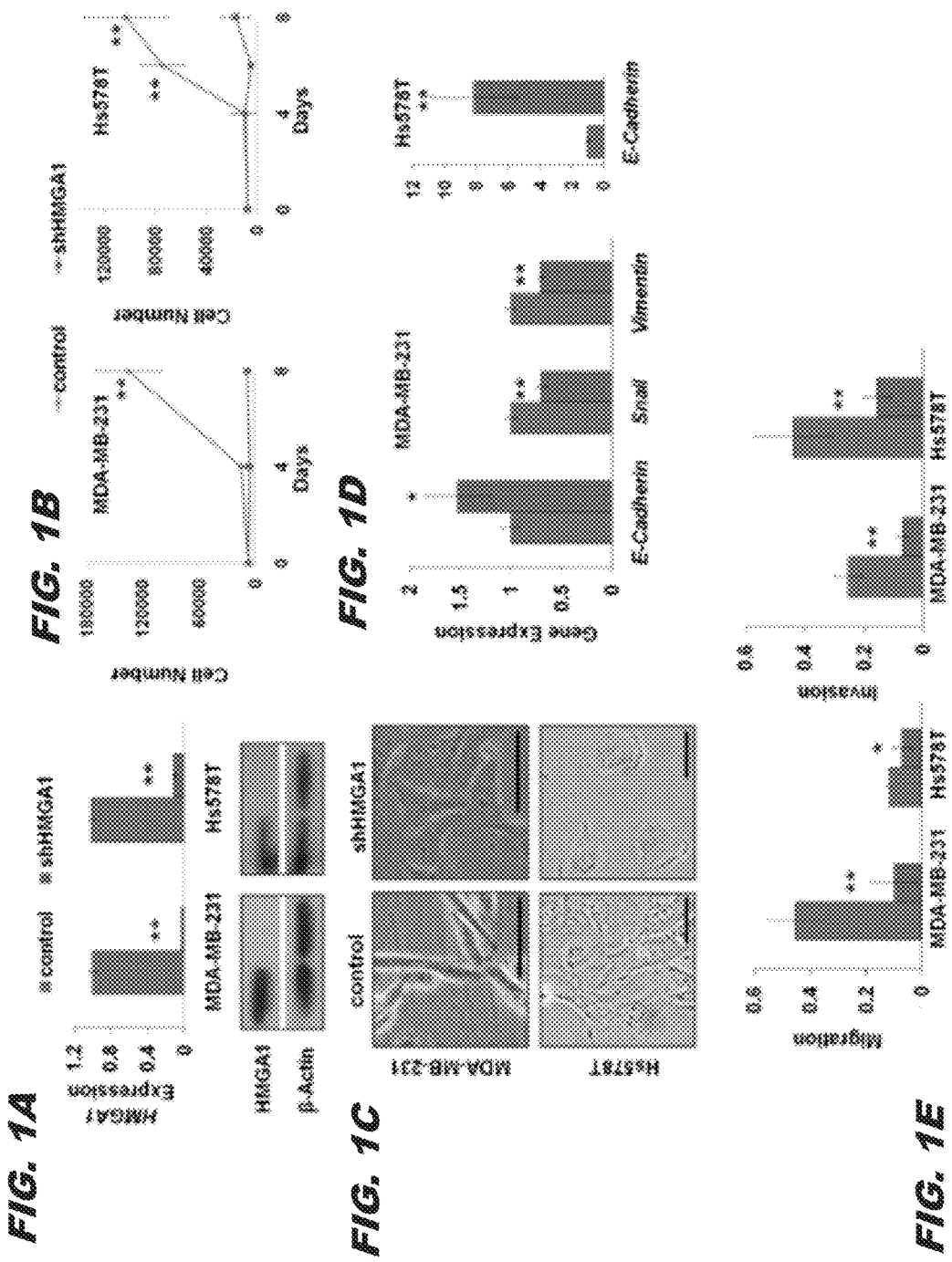

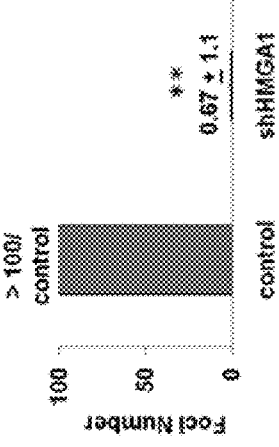
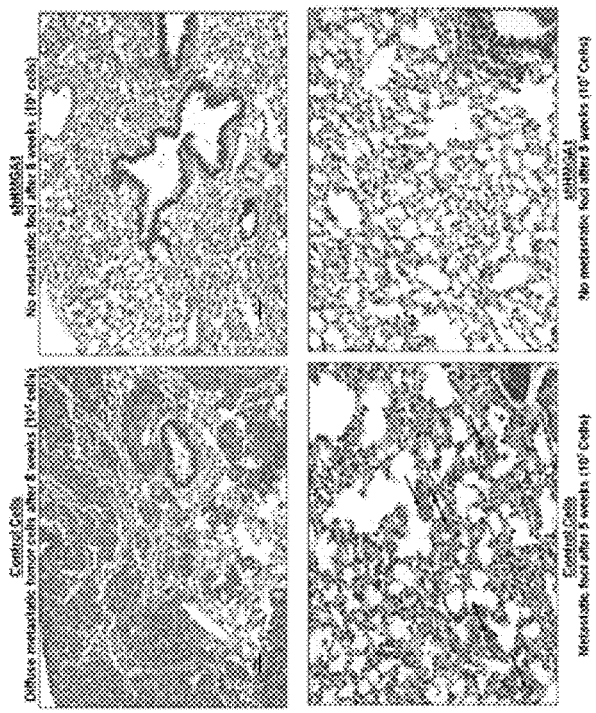
FIG. 2A  FIG. 2B  FIG. 2C  FIG. 2D

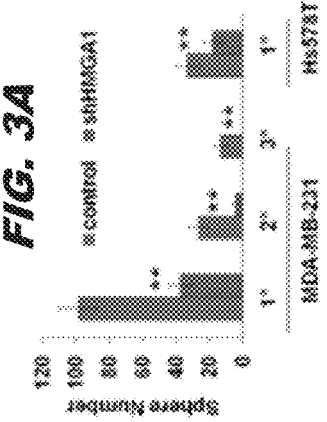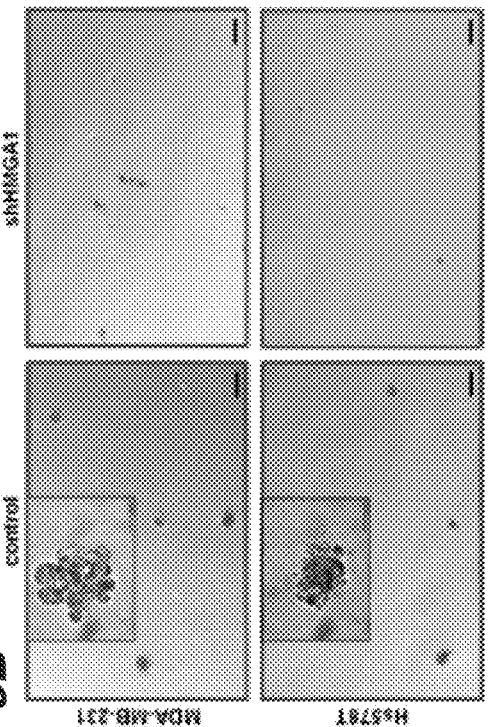
FIG. 3A FIG. 3B FIG. 3C

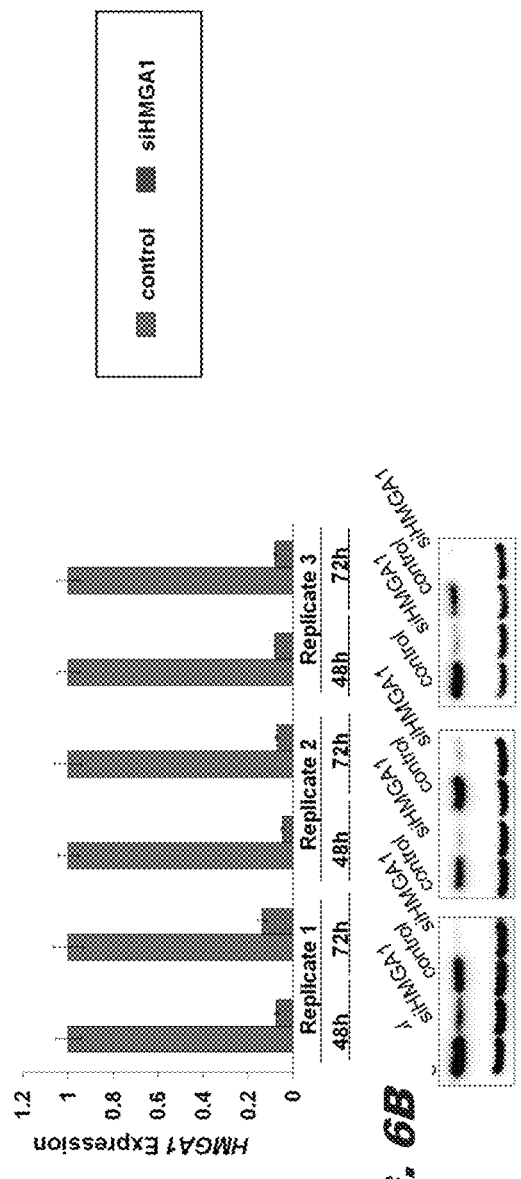
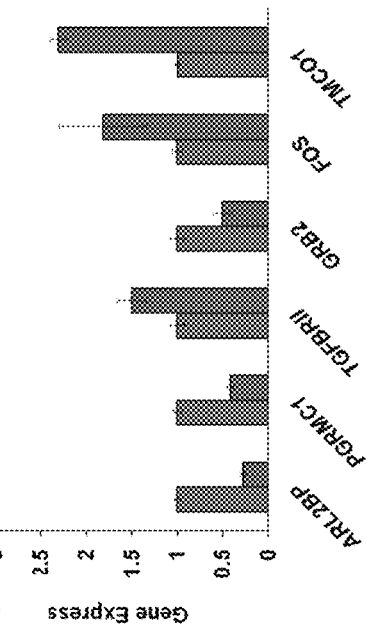
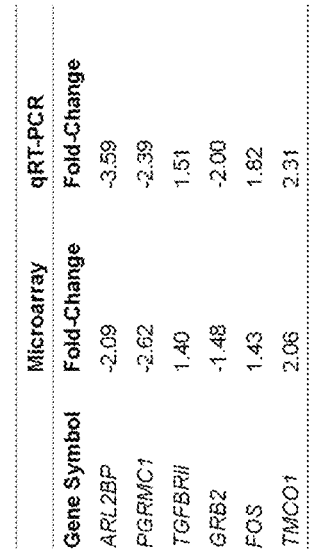
FIG. 6A
FIG. 6B
FIG. 6C
FIG. 6D

FIG. 10A
FIG. 10B
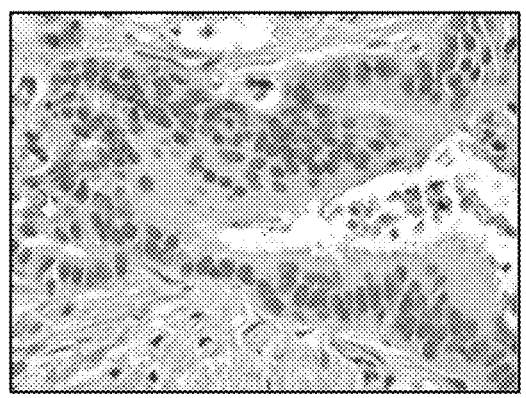
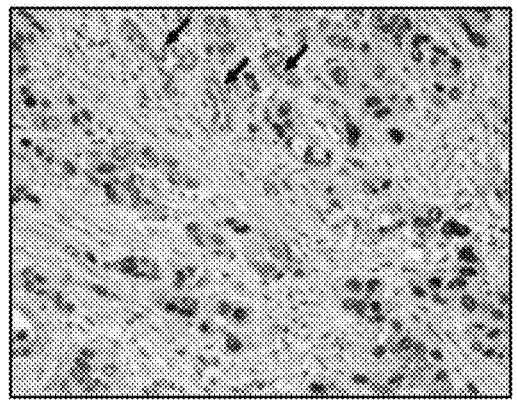
FIG. 10C
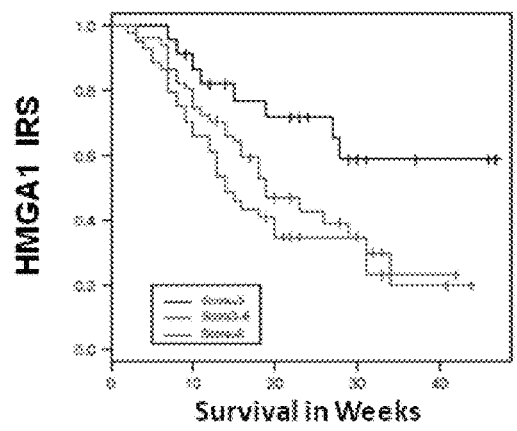

*FIG. 12A*
*FIG. 12B*
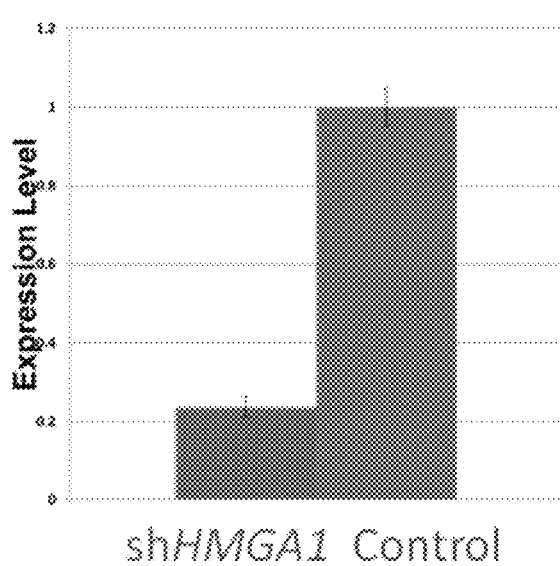
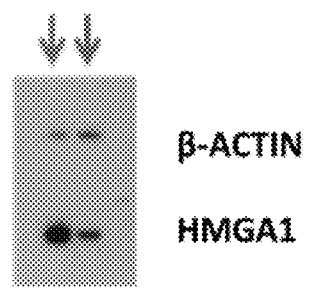

*FIG. 14A*
*FIG. 14B*
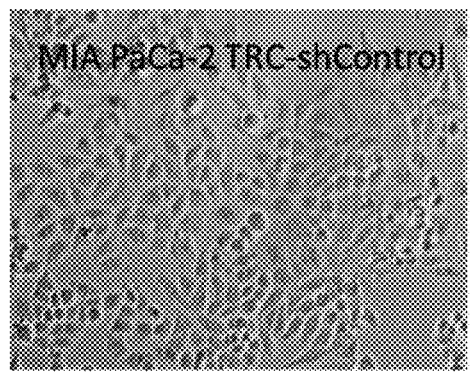
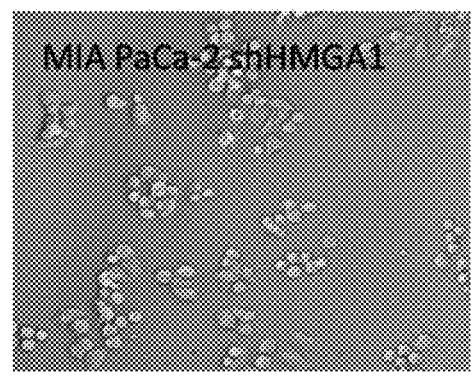
Control
shHMGA1

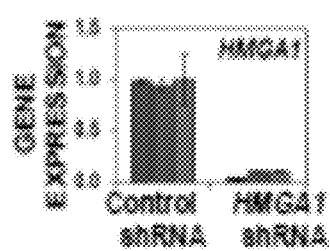
FIG. 16A
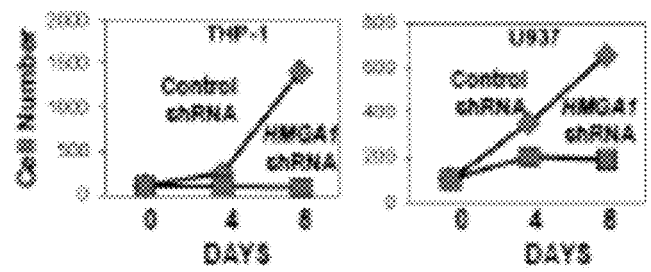
FIG. 16B
FIG. 16C
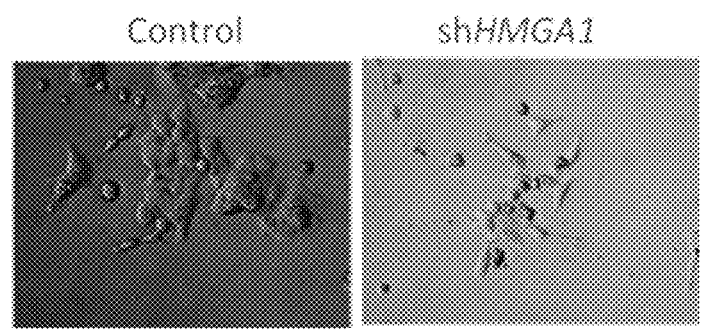

*FIG. 18A*
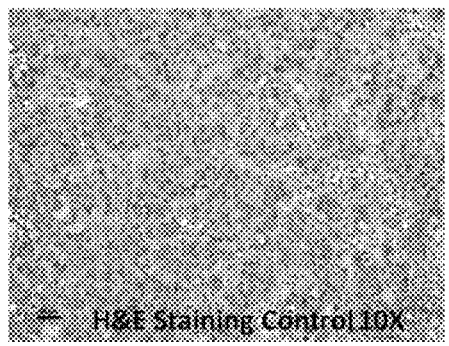
*FIG. 18B*
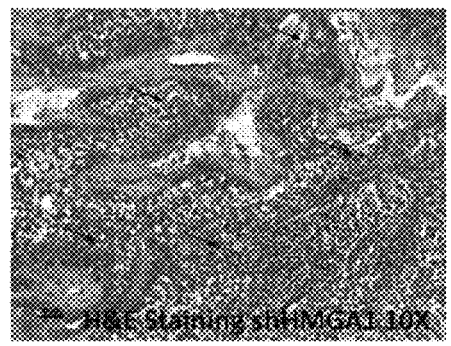
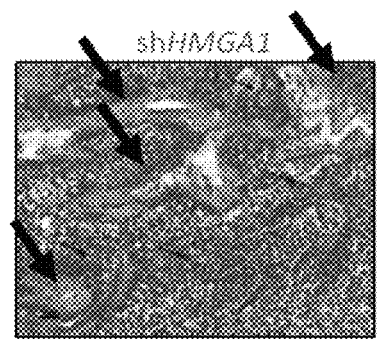
*FIG. 18C*
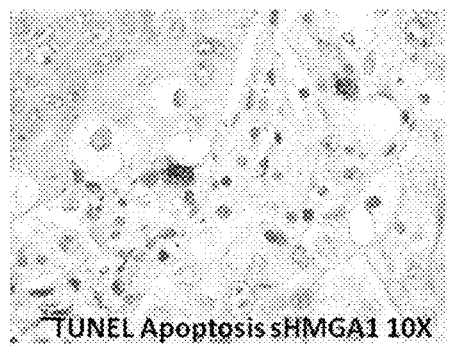

METHODS OF INHIBITING CANCER STEM CELLS WITH HMGA1 INHIBITORS

CROSS-REFERENCE TO RELATED APPLICATIONS

This application is a divisional of U.S. Utility application Ser. No. 14/701,586 filed May 1, 2015, which claims the benefit of U.S. Provisional Application No. 61/987,264, filed May 1, 2014, which are incorporated herein by reference in their entirety.

FEDERALLY SPONSORED RESEARCH OR DEVELOPMENT

This invention was made with government support under CA149550 awarded by the National Institutes of Health (NIH). The government has certain rights in the invention.

INCORPORATION-BY-REFERENCE OF MATERIAL SUBMITTED ELECTRONICALLY

This application contains a sequence listing. It has been submitted electronically via EFS-Web as an ASCII text file entitled "111232-00396_ST25.txt". The sequence listing is 390 bytes in size, and was created on Apr. 29, 2015. It is hereby incorporated by reference in its entirety.

FIELD OF INVENTION

The presently disclosed subject matter relates to the field of molecular biology, and particularly to methods of inhibiting cancer stem cells and growth of aggressive and/or poorly differentiated metastatic tumors with HMGA1 inhibitors.

BACKGROUND

Despite advances in the ability to detect and treat breast cancer, it remains a leading cause of death in women with cancer, and the incidence is rising (Siegel et al. (2013) *CA Cancer J. Clin.* 63:11-30). Approximately 15-20% of all cases are classified as triple-negative breast cancer, a subtype that is frequently associated with rapid progression and poor outcomes (Siegel et al. (2013) *CA Cancer J. Clin.* 63:11-30; Lee et al. (2010) *Cancer Biol. Ther.* 9:1017-1024). Triple-negative breast cancer refers to the lack of detectable markers for the estrogen receptor (ER), progesterone receptor (PR), and Her2/neu amplification.

Treatment of patients with triple-negative breast cancer has been challenging due to the heterogeneity of the disease and the absence of well-defined molecular targets (Pegram et al. (1998) *J. Clin. Oncol.* 16:2659-2671; Wiggans et al. (1979) *Cancer Chemother. Pharmacol.* 3:45-48; Carey et al. (2007) *Clin. Cancer Res.* 13:2329-2334). Triple-negative breast cancer tumors are generally larger in size, are of higher grade, have lymph node involvement at diagnosis, and are biologically more aggressive than other types of breast cancer tumors (Haffty (2006) *J. Clin. Oncol.* 24:5652-5657). Despite having higher rates of clinical response to presurgical (neoadjuvant) chemotherapy, triple-negative breast cancer patients have a higher rate of distant recurrence and a poorer prognosis than women with other breast cancer subtypes (Haffty (2006) *J. Clin. Oncol.* 24:5652-5657; Dent et al. (2007) *Clin. Cancer Res.* 13:4429-4434). These tumors do not respond to the most effective and least toxic therapies, including hormonal therapy (tamoxifen) or herceptin. Less than 30% of women with metastatic triple-negative breast cancer survive 5 years, and almost all die of their disease despite adjuvant chemotherapy, which is the mainstay of treatment (Dent et al. (2007) *Clin. Cancer Res.* 13:4429-4434).

SUMMARY

The presently disclosed subject matter relates to methods of inhibiting cancer stem cells using HMGA1 inhibitors. In an aspect, the presently disclosed subject matter provides a method of inhibiting at least one cancer stem cell, the method comprising contacting the at least one cancer stem cell with an effective amount of at least one HMGA1 inhibitor. In some embodiments, inhibiting the at least one cancer stem cell is selected from the group consisting of: i) inhibiting proliferation of the at least one cancer stem cell; ii) inhibiting self-renewal of the at least one cancer stem cell; iii) inhibiting anchorage-independent growth of the at least one cancer stem cell; iv) inhibiting migration of the at least one cancer stem cell; v) inhibiting invasion of the at least one cancer stem cell; vi) reprogramming the at least one cancer stem cell from a stem-like state that is refractory to apoptosis to a non stem-like state that is susceptible to apoptosis; and vii) combinations thereof. In some embodiments, at least one cancer stem cell is in an aggressive and/or poorly differentiated metastatic tumor, and inhibiting the at least one cancer stem cell inhibits at least one of: i) growth of the aggressive and/or poorly differentiated metastatic tumor; ii) proliferation of the aggressive and/or poorly differentiated metastatic tumor; iii) migration of the aggressive and/or poorly differentiated metastatic tumor; iv) invasion of the aggressive and/or poorly differentiated metastatic tumor; v) initiation of new aggressive and/or poorly differentiated metastatic tumors, and vi) combinations thereof. In some embodiments, at least one cancer stem cell expresses greater levels of HMGA1 as compared to non-stem cancer cells in the aggressive and/or poorly differentiated metastatic tumor. In some embodiments, at least one cancer stem cell is selected from the group consisting of a triple-negative breast cancer cell, a pancreatic ductal adenocarcinoma cell, a colorectal cancer cell, and a leukemia cell. In some embodiments, at least one HMGA1 inhibitor reduces the expression level and/or activity of HMGA1. In some embodiments, at least one HGMA1 inhibitor is an RNA interfering agent. In some embodiments, at least one HMGA1 inhibitor is an shRNA. In some embodiments, the shRNA targets the nucleotide sequence of SEQ ID NO: 1. In some embodiments, the method includes contacting the at least one cancer stem cell with a chemotherapeutic agent. In some embodiments, the chemotherapeutic agent is gemcitabine. In some embodiments, at least one cancer stem cell is contacted in a subject. In some embodiments, the subject is a human subject.

In certain aspects, the presently disclosed subject matter provides a method of treating an aggressive and/or poorly differentiated metastatic cancer in a subject in need thereof comprising administering a therapeutically effective amount of at least one HMGA1 inhibitor to the subject. In some embodiments, the aggressive and/or poorly differentiated metastatic cancer is selected from the group consisting of triple-negative breast cancer, pancreatic ductal adenocarcinoma cell, colorectal cancer cell, and leukemia. In some embodiments, the aggressive and/or poorly differentiated metastatic cancer comprises at least one cancer stem cell that overexpresses HMGA1 protein. In some embodiments, the method includes selecting the subject for treatment of the aggressive and/or poorly differentiated metastatic cancer with the at least one HMGA1 inhibitor. In some embodiments, selecting the subject for treatment of the aggressive and/or poorly differentiated metastatic cancer comprises: (i) obtaining a biological sample comprising cells from the aggressive and/or poorly differentiated metastatic cancer; (ii) assaying the level of HMGA1 expression in the cells from the aggressive and/or poorly differentiated metastatic cancer; (iii) comparing the level of HMGA1 expression in the cells to the level of HMGA1 expression in a normal control cell; and (iv) selecting the subject for treatment of the aggressive and/or poorly differentiated metastatic cancer with the at least one HMGA1 inhibitor if the level of HMGA1 expression in the cells is greater than the level of HMGA1 expression in the normal control cell. In some embodiments, the biological sample is selected from the group consisting of a breast tissue sample, a pancreatic tissue sample, a colon tissue sample, and a bone marrow tissue sample. In some embodiments, at least some of the cells from the aggressive and/or poorly differentiated metastatic cancer comprise cancer stem cells. In some embodiments, the at least one HMGA1 inhibitor reduces the expression level and/or activity of HMGA1. In some embodiments, the at least one HMGA1 inhibitor is formulated for delivery in a nanoparticle. In some embodiments, the at least one HGMA1 inhibitor is an RNA interfering agent. In some embodiments, the at least one HMGA1 inhibitor is an shRNA. In some embodiments, the shRNA targets the nucleotide sequence of SEQ ID NO: 1. In some embodiments, the shRNA is formulated for delivery in a nanoparticle. In some embodiments, the subject is a human subject. In some embodiments, the method includes administering an effective amount of a chemotherapeutic agent to the subject. In some embodiments, the chemotherapeutic agent is gemcitabine.

In other aspects, the presently disclosed subject matter provides a method of selecting a subject with an aggressive and/or poorly differentiated metastatic cancer for treatment with at least one HMGA1 inhibitor, the method comprising: (a) obtaining a biological sample from the subject, wherein the biological sample comprises cells from the aggressive and/or poorly differentiated metastatic cancer; (b) determining the level of expression of HMGA1 in the biological sample; (c) comparing the level of expression of HMGA1 in the biological sample with the level of expression of HMGA1 in a control sample; and (d) selecting the subject with aggressive and/or poorly differentiated metastatic cancer for treatment with at least one HMGA1 inhibitor when the level of HMGA1 expression in the biological sample is greater than the level of HMGA1 expression in the control sample. In some embodiments, the biological sample is selected from the group consisting of a breast tissue sample, a pancreatic tissue sample, a colon tissue sample, and a bone marrow tissue sample. In some embodiments, the aggressive and/or poorly differentiated metastatic cancer is selected from the group consisting of triple-negative breast cancer, pancreatic ductal adenocarcinoma cell, colorectal cancer cell, and leukemia. In some embodiments, subject is a human subject. In some embodiments, the method includes treating the subject with aggressive and/or poorly differentiated metastatic cancer by administering an effective amount of at least one HMGA1 inhibitor (e.g., an shRNA, e.g., targeting SEQ ID NO: 1) to the subject. In some embodiments, the method includes administering an effective amount of at least one chemotherapeutic agent to the subject.

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

The practice of the present invention will typically employ, unless otherwise indicated, conventional techniques of cell biology, cell culture, molecular biology, transgenic biology, microbiology, recombinant nucleic acid (e.g., DNA) technology, immunology, and RNA interference (RNAi) which are within the skill of the art. Non-limiting descriptions of certain of these techniques are found in the following publications: Ausubel, F., et al., (eds.), Current Protocols in Molecular Biology, Current Protocols in Immunology, Current Protocols in Protein Science, and Current Protocols in Cell Biology, all John Wiley & Sons, N.Y., edition as of December 2008; Sambrook. Russell, and Sambrook, Molecular Cloning: A Laboratory Manual, 3rd ed., Cold Spring Harbor Laboratory Press, Cold Spring Harbor, 2001; Harlow, E. and Lane, D., Antibodies—A Laboratory Manual, Cold Spring Harbor Laboratory Press, Cold Spring Harbor, 1988; Freshney, R. I., "Culture of Animal Cells, A Manual of Basic Technique", 5th ed., John Wiley & Sons, Hoboken, N.J., 2005. Non-limiting information regarding therapeutic agents and human diseases is found in Goodman and Gilman's The Pharmacological Basis of Therapeutics, 11th Ed., McGraw Hill, 2005, Katzung, B. (ed.) Basic and Clinical Pharmacology, McGraw-Hill/Appleton & Lange; 10th ed. (2006) or 11th edition (July 2009). Non-limiting information regarding genes and genetic disorders is found in McKusick, V. A.: Mendelian Inheritance in Man. A Catalog of Human Genes and Genetic Disorders. Baltimore: Johns Hopkins University Press, 1998 (12th edition) or the more recent online database: Online Mendelian Inheritance in Man, OMIM™. McKusick-Nathans Institute of Genetic Medicine, Johns Hopkins University (Baltimore, Md.) and National Center for Biotechnology Information, National Library of Medicine (Bethesda. Md.), as of May 1, 2010, World Wide Web URL: http://www.ncbi.nlm.nih.gov/omim/ and in Online Mendelian Inheritance in Animals (OMIA), a database of genes, inherited disorders and traits in animal species (other than human and mouse), at http://omia.angis.org.au/contact.shtml. All patents, patent applications, and other publications (e.g., scientific articles, books, websites, and databases) mentioned herein are incorporated by reference in their entirety. In case of a conflict between the specification and any of the incorporated references, the specification (including any amendments thereof, which may be based on an incorporated reference), shall control. Standard art-accepted meanings of terms are used herein unless indicated otherwise. Standard abbreviations for various terms are used herein.

BRIEF DESCRIPTION OF THE FIGURES

Figure 4A:
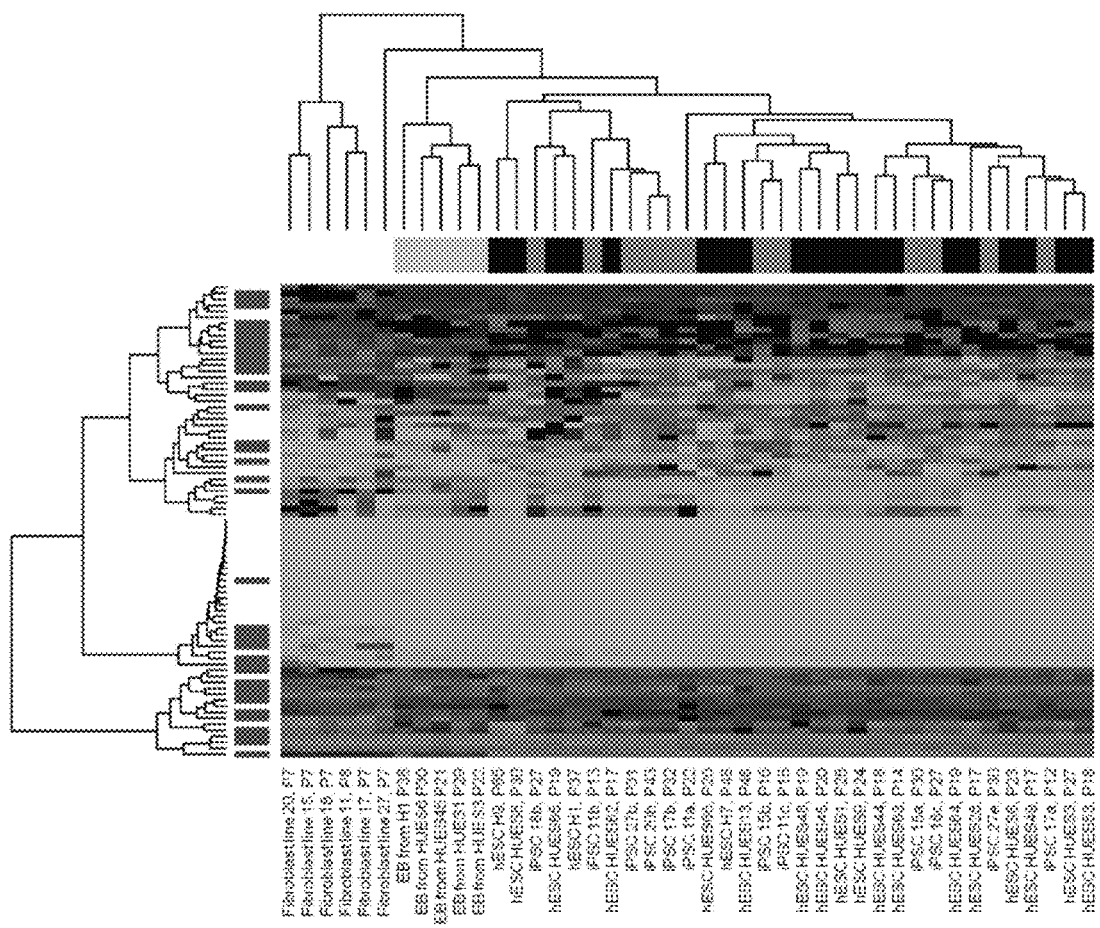
Figure 4B:
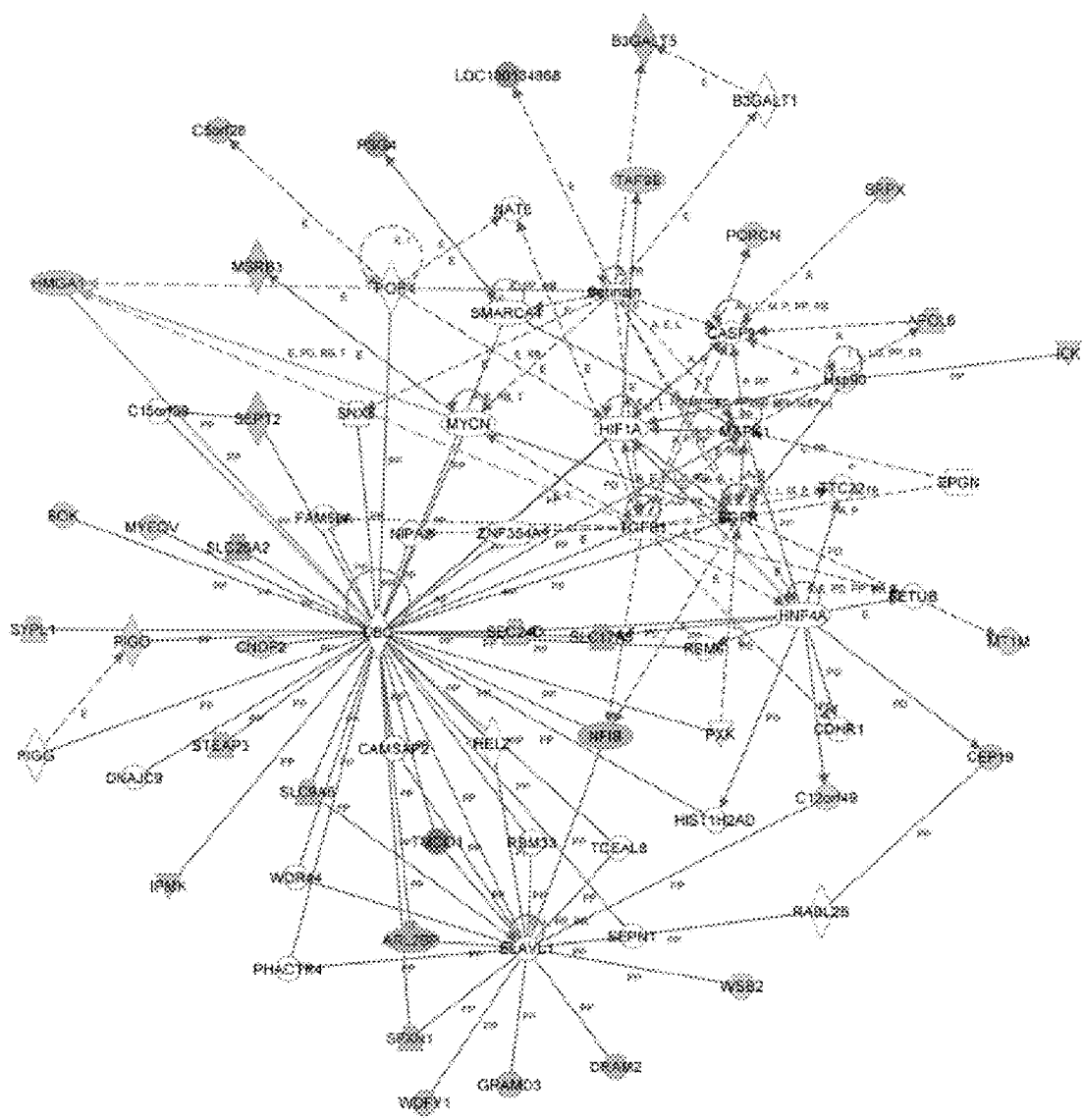
Figure 5A:
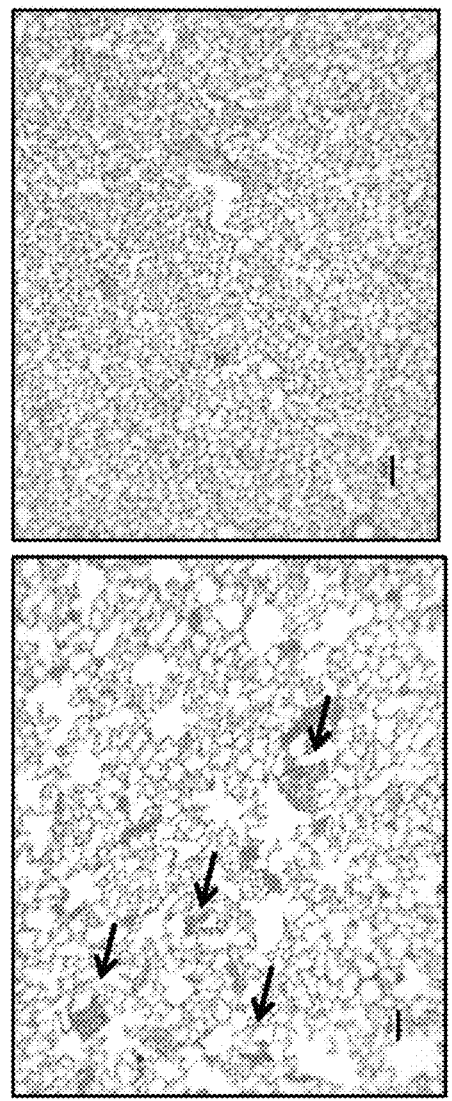
Figure 5B:
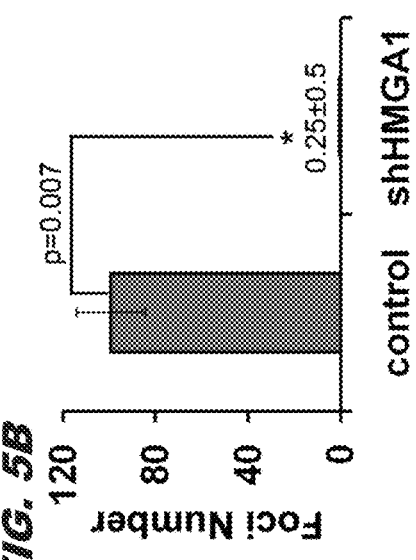
Figure 7:
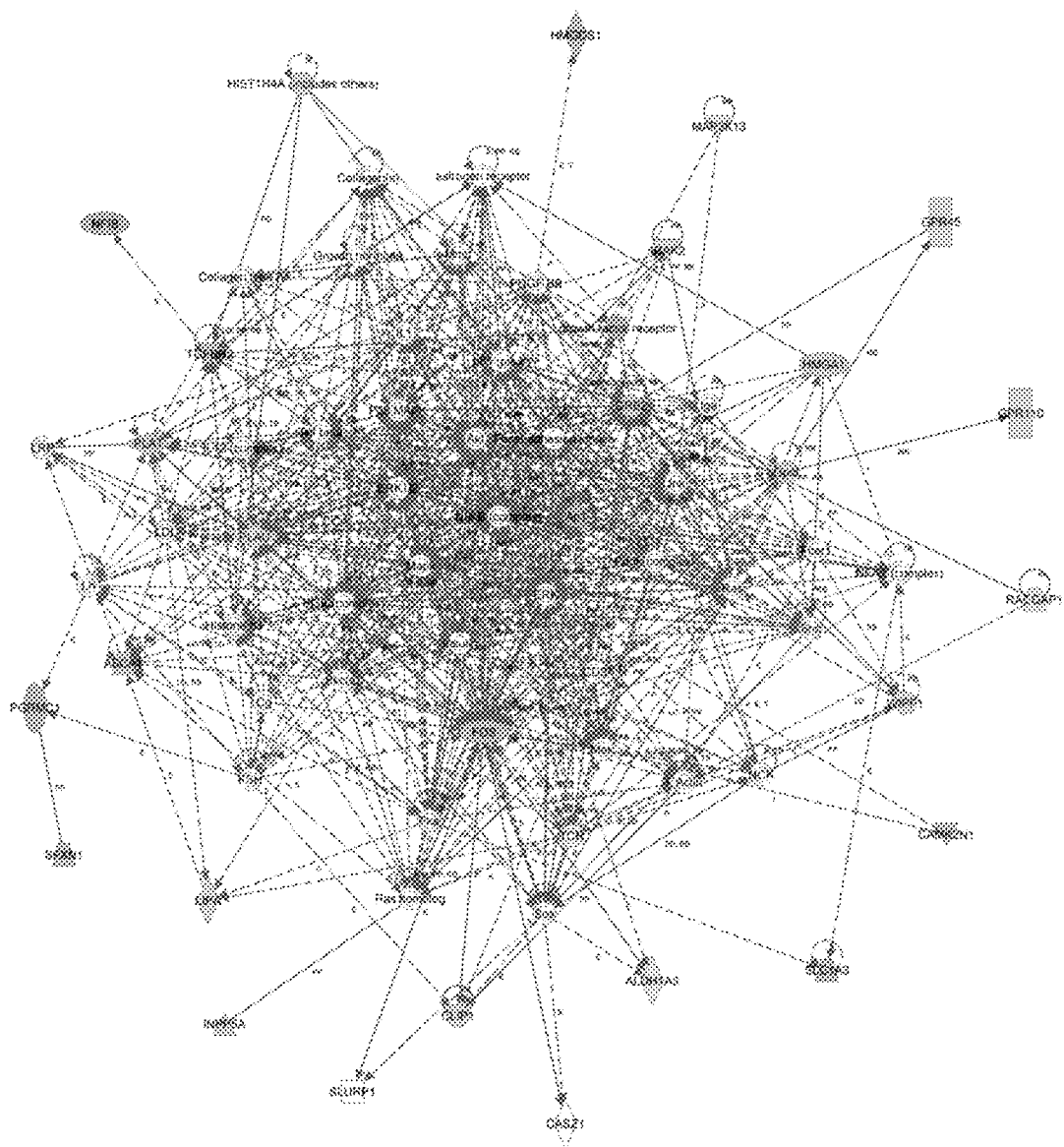
Figure 8:
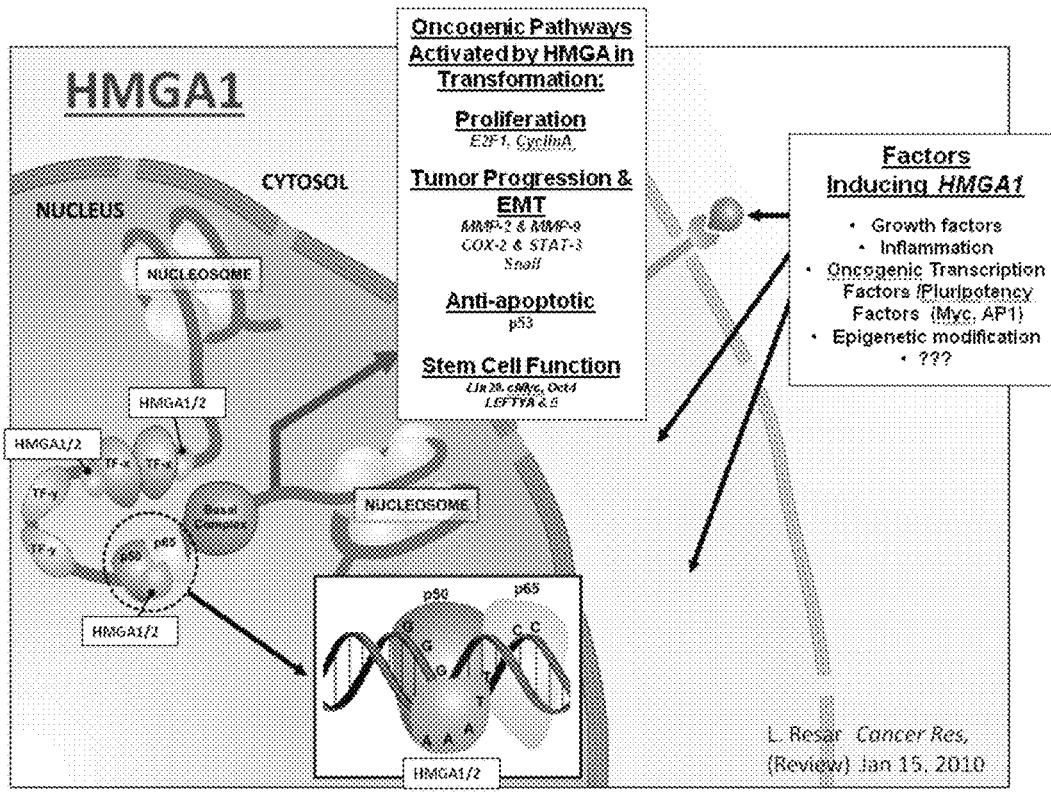
Figure 9:
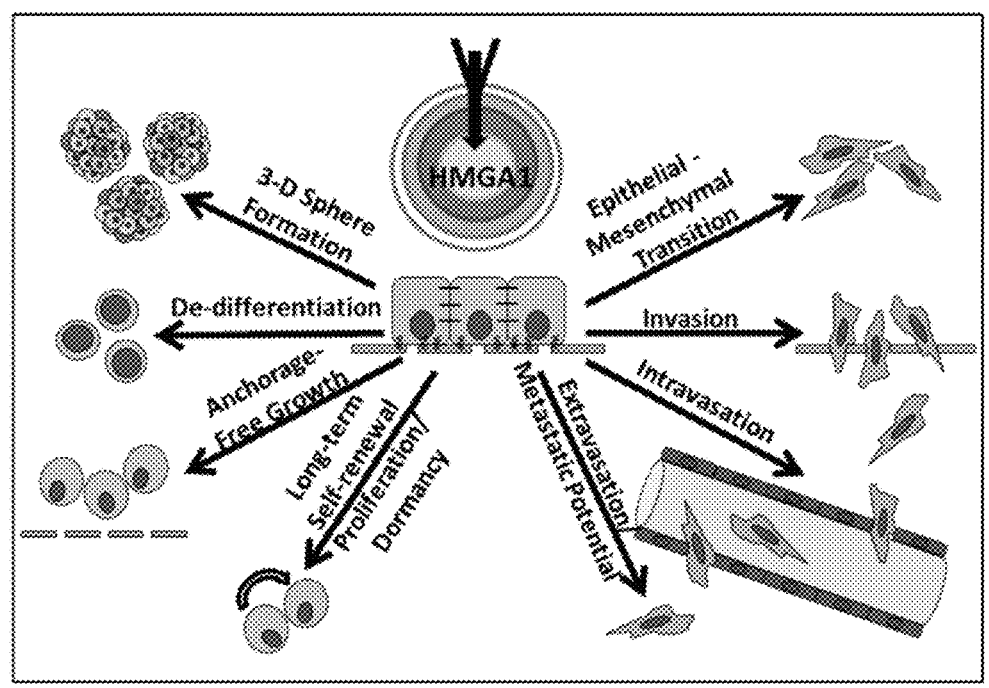
Figure 11:
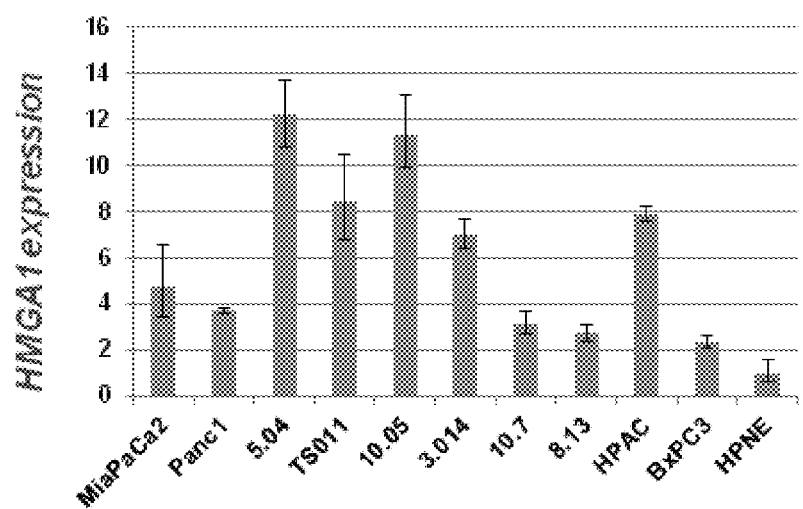
Figure 13:
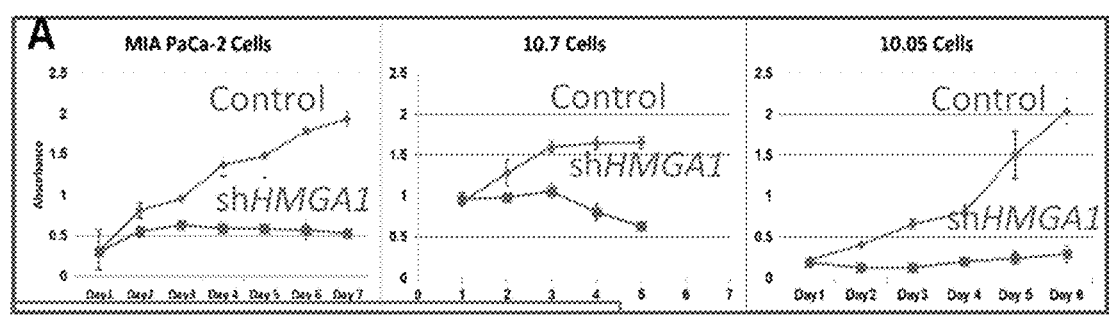
Figure 15A:
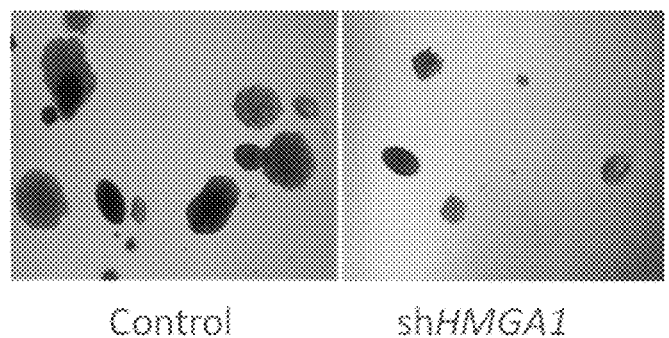
Figure 15B:
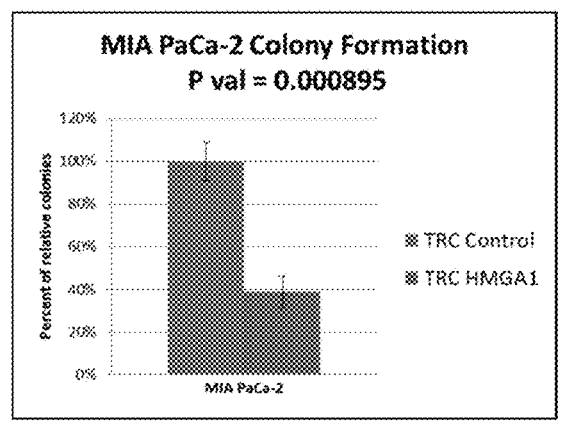
Figure 15C:
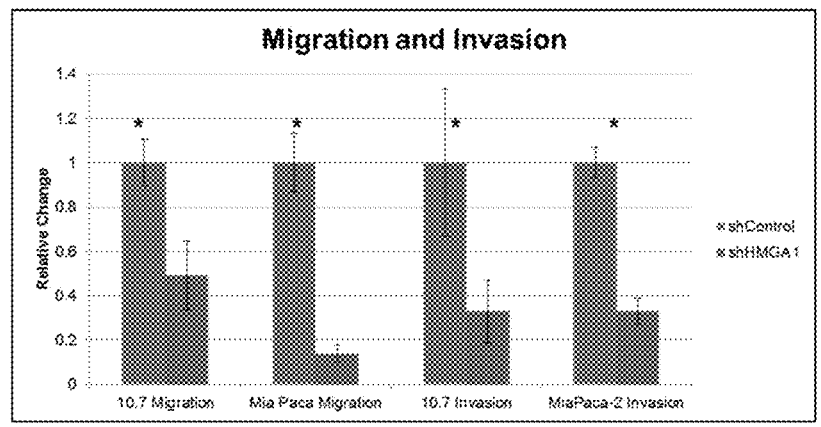
Figure 17:
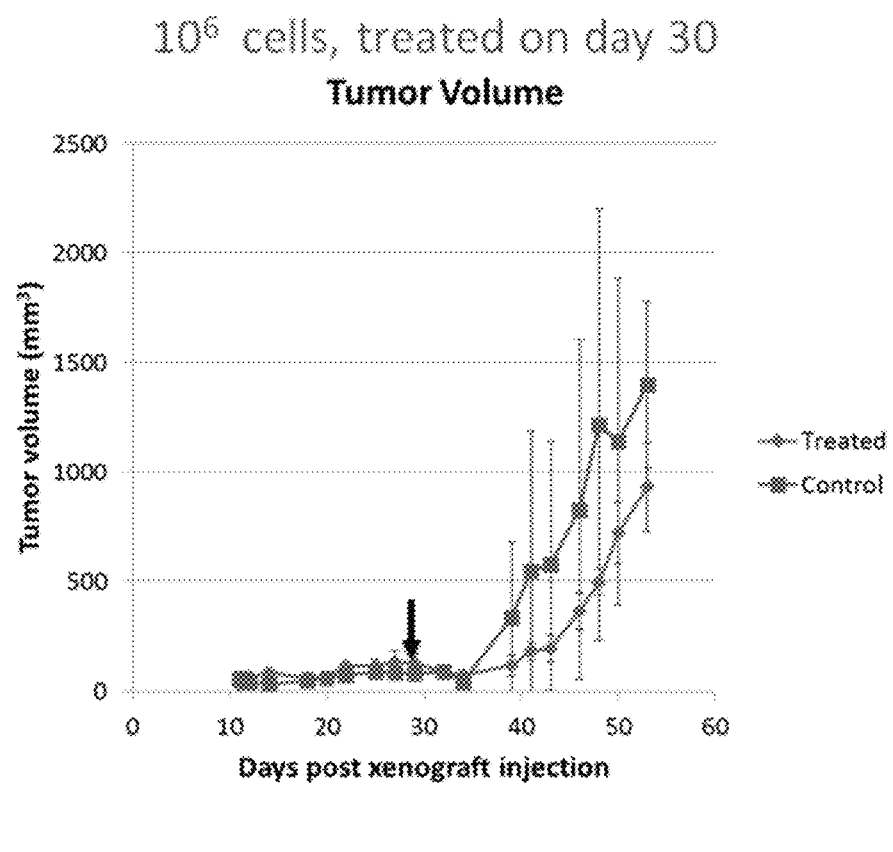

Having thus described the presently disclosed subject matter in general terms, reference will now be made to the accompanying Figures, which are not necessarily drawn to scale, and wherein:

FIG. 1A, FIG. 1B, FIG. 1C, FIG. 1D and FIG. 1E show that silencing HMGA1 expression halts cell growth and induces dramatic changes in cell morphology and gene expression: FIG. 1A) lentiviral-mediated delivery of shRNA to HMGA1 (denoted shHMGA1) results in a marked decrease in HMGA1 mRNA and protein in triple-negative breast cancer cell lines (MDA-MB-231, Hs578T); FIG. 1B)

proliferation is disrupted in cancer cell lines following silencing of HMGA1; FIG. 1C) mesenchymal, fibroblast-like cancer cells undergo dramatic morphologic changes within 4 days after treatment with shHMGA1; striking changes were observed in MDA-MB-231 (top panels) and Hs578T cells (bottom panels); bar: 50 um; FIG. 1D) alterations in EMT genes with silencing of HMGA1; and FIG. 1E) migration and invasion is decreased with silencing of HMGA1. *P<0.05; **P<0.01;

FIG. 2A, FIG. 2B, FIG. 2C and FIG. 2D show that silencing HMGA1 interferes with orthotopic tumorigenicity and metastatic progression: FIG. 2A) silencing HMGA1 impairs orthotopic tumorigenicity; tumor volumes±standard deviations are shown; no tumors formed from shHMGA1 cells when $10^4$ cells were implanted (for injections with $10^4$ cells, n=3 for control or shHMGA1 cells; for injections with $10^5$ cells, n=5 for control and n=8 for shHMGA1 cells; and for injections with $10^7$ cells, n=3 for control and shHMGA1 cells; FIG. 2B) metastatic progression is almost completely abrogated in cells that do not express HMGA1; this graph shows the number metastatic foci to the lung 5 weeks following implantation of MDA-MB-231 cells ($10^7$) into mammary fat pads following treatment with control shRNA or shHMGA1; FIG. 2C) the top photographs show the lungs 8 weeks following implantation into mammary fat pads; there are coalescing sheets of metastatic tumor cells in the lungs of mice injected with control cells (left) as compared to mice injected with shHMGA1 cells (right); due to the widespread tumor cells, individual foci could not be counted; bar: 50 um; and FIG. 2D) the bottom panels show multiple, discreet foci in the lungs 5 weeks following implantation of control cells into mammary fat pads (left) as compared to mice injected with shHMGA1 cells (right). *P<0.05; **P<0.0001;

FIG. 3A, FIG. 3B and FIG. 3C show that silencing HMGA1 blocks mammosphere formation and depletes tumor-initiator cells: FIG. 3A) silencing HMGA1 blocks mammosphere formation in MDA-MB-231 cells (1°, 2°, 3°) and Hs578T cells (1°); FIG. 3B) photographs of mammospheres following treatment of breast cancer cells with control or shHMGA1 silencing HMGA1 significantly inhibits mammosphere formation in MDA-MB-231 and Hs578T cells; bars: 200 um (large panels) and 50 um (insets); and FIG. 3C) tumor numbers at limiting dilutions show that silencing HMGA1 depletes the tumor initiator/cancer stem cells in MDA-MB-231 cells; note that no tumors formed following injection of $10^4$ cells treated with shHMGA1, while tumors formed in all cases when control cells were injected; both tumor frequency and tumor volumes (±standard deviations) are shown. *P<0.05; **P<0.01;

FIG. 4A and FIG. 4B show that the HMGA1 signature is enriched in pluripotent stem cells, including embryonic and induced pluripotent stem cells; FIG. 4A shows the HMGA signature derived from genes with the greatest expression changes in the control versus HMGA1 knock-down cells displayed as a heat map. Green depicts down-regulation in expression, while red depicts up-regulation; black denotes little or no change in expression. The HMGA1 signature overlaps with pluripotent stem cell genes that distinguish human embryonic stem cells (hESCs) and induced pluripotent stem cells (iPSCs) from fibroblasts and embryoid bodies (EB). Genes (n=63) were selected for the greatest changes in expression in the breast cancer cell lines with HMGA1 knock-down as compared to the control breast cancer lines (FIG. 5). In a hierarchical clustering of fibroblasts, hESCs, iPSCs, and EBs derived from the hESCs, these genes distinguish samples by type. The majority of the HMGA1 signature genes, represented in blue along the left margin, are significantly differentially expressed between fibroblasts and human pluripotent stem cells (hESC/iPSCs; p<0.001); and FIG. 4B shows a HMGA1 network derived from the list of differentially expressed genes using Ingenuity Pathway Analysis (IPA) with microarray gene expression data from control and HMGA1 knock-down in MDA-MB-231 cells. From among 63 differentially expressed genes as the focus gene set, the highest-scoring network was Embryonic Development, Tissue Development, and Cellular Development (score=69). Red nodes indicate up-regulation; green nodes indicate down-regulation. Arrows and lines denote interactions between specific genes within the network. A, activation; E, expression regulation; I, inhibition; L, proteolysis; LO, localization; M, biochemical modification; MB, membership of a group or complex; P, phosphorylation; PD, protein-DNA interaction; PP, protein-protein interaction; PR, protein-RNA interaction; RB, regulation of binding; RE, reaction; T, transcription; TR, translocation:

FIG. 5A and FIG. 5B show that silencing HMGA1 in MDA-MB-231 blocks the formation of foci to the lung following tail vein injections: FIG. 5A depicts lung foci enumerated 3 weeks following tail vein injections of control or shHMGA1 MDA-MB-231 cells (n=3 for control mice; n=4 for shHMGA1 mice); and FIG. 5B is a graph of the mean number of tumor foci±standard deviation, which shows a striking decrease in foci following injection of shHMGA1 MDA-MB-231 cells as compared to controls (p=0.007);

FIG. 6A, FIG. 6B, FIG. 6C and FIG. 6D show that silencing HMGA1 in MDA-MB-231 results in significant repression in HMGA1 mRNA and protein, with alterations in gene expression: FIG. 6A demonstrates that independent replicate experiments of MDA-MB-231 cells with or without HMGA1 knock-down result in silencing HMGA1 at the level of mRNA; FIG. 6B demonstrates that HMGA1 protein is also repressed following treatment with siRNA; FIG. 6C is a validation of genes in the HMGA1 signature which shows that gene expression assessed by quantitative RT-PCR (qRT-PCR) parallels that of the microarray results; and FIG. 6D is a table comparing differential expression of the HMGA1 signature identified by microarray and qRT-PCR;

FIG. 7 shows the HMGA1 network derived from differentially expressed genes in MDA-MB-231 with or without HMGA1 knock-down. From among 63 differentially expressed genes as the focus gene set, the second highest-scoring network was Cardiovascular Disease, Cell Death and Survival, and Nervous System Development and Function (score=46). Colors, arrows, lines and abbreviations are described under FIG. 4B. NF-κB, ERK, and MAPK are major nodes, which have been identified in prior studies of global gene expression profiles mediated by HMGA1 (Schuldenfrei et al. (2011) *BMC Genomics* 12:549):

FIG. 8 demonstrates the oncogenic pathways activated by HMGA;

FIG. 9 demonstrates the targeting of HMGA1 in cancer stem cells:

FIG. 10A, FIG. 10B, and FIG. 10C demonstrate that HMGA1 correlates with poor differentiation and decreased survival in pancreatic cancer; FIG. 10A shows a well-differentiated tumor with low levels of HMGA1 immunoreactivity; FIG. 10B shows a high-grade, poorly differentiated tumor with high immunoreactivity. Patient survival (FIG. 10C) is decreased with high levels of HMGA1:

FIG. 11 demonstrates HMGA1 expression levels in different pancreatic ductal adenocarcinoma cell (PDAC) lines; gene expression was assessed via quantitative RT-PCR (qRT-PCR);

FIG. 12A and FIG. 12B demonstrate that HMGA1 is silenced by short hairpin RNA as seen by expression levels (via qRT-PCR) of HMGA1 with (red) and without (blue) shHMGA1; FIG. 12B shows protein levels by Western blot;

FIG. 13 demonstrates that silencing HMGA1 via shHMGA disrupts cell proliferation in three PDAC cell lines (red), including two patient-derived cell lines, as compared to the control (blue);

FIG. 14A and FIG. 14B demonstrate that silencing HMGA1 alters morphology of pancreatic ductal adenocarcinoma cells. FIG. 14A shows morphology of control cells not treated with the HMGA1 shRNA (spindle-shaped, mesenchymal cells) as compared to the morphology of pancreatic ductal adenocarcinoma cells treated with shRNA targeting HMGA1 (rounded, more cuboidal-shaped cells; FIG. 14B):

FIG. 15A, FIG. 15B and FIG. 15C demonstrate that silencing HMGA1 via shHMGA blocks 3D sphere formation (FIG. 15A), PDAC colony formation (FIG. 1B), and migration and invasion (FIG. 15C);

FIG. 16A, FIG. 16B, and FIG. 16C demonstrate that silencing is cytotoxic in acute myeloid leukemia (AML) cell lines and that silencing in colorectal cancer cells halts proliferation and alters cell morphology. FIG. 16A shows silencing of HMGA1 in three AML cell lines and FIG. 16B shows marked cytotoxicity in HMGA1 knock-down cells. FIG. 16C shows that silencing HMGA1 in colorectal cancer cells halts proliferation and alters cell morphology;

FIG. 17 demonstrates nanoparticle shRNA treatment in PDAC cell line 10.7 xenografts. The PDAC cell line was injected into mice on tumors allowed to grow. By day 30, mice were treated with nanoparticles to deliver shRNA to the tumors; and FIG. 18A, FIG. 18B, and FIG. 18C demonstrate vacuolated cytoplasm of most tumor cells, individual cell death (arrows) and area of necrosis (outlined) in a shHMGA1 treated tumor.

The patent or application file contains at least one drawing executed in color. Copies of this patent or patent application publication with color drawings will be provided by the Office upon request and payment of the necessary fee.

DETAILED DESCRIPTION

The presently disclosed subject matter now will be described more fully hereinafter with reference to the accompanying Figures, in which some, but not all embodiments of the presently disclosed subject matter are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

Emerging evidence suggests that tumor cells metastasize by co-opting stem cell transcriptional networks, although the molecular underpinnings of this process are poorly understood. Recent studies have identified the high mobility group A1 (HMGA1) oncogene (Entrez Gene ID: 3159) as a key factor enriched in embryonic stem cells, adult stem cells, and refractory or high-grade/poorly differentiated tumors (Ben-Porath et al. (2008) *Nat. Genet.* 40:499-507; Resar (2010) *Cancer Research* 70:436-439; Chou et al. (2011) *Cell Res.* 21:518-529; Zhou et al. (2001) *Proc. Natl. Acad. Sci. USA* 98:13966-13971; Karp et al. (2011) *Blood* 117:3302-3310; Nelson et al. (2011) *Leuk Lymphoma* 52:1999-2006; Schuldenfrei et al. (2011) *BMC Genomics* 12:549; Belton et al. (2012) *PloS One* 7:e30034; Shah and Resar (2012) *Histol. Histopathol.* 27:567-579; Wood et al. (2000) *Mol. Cell. Biol.* 20:5490-5502; Pedulla et al. (2001) *Gene* 271: 51-58; Reeves and Beckerbauer (2001) *Biochim. Biophys. Acta* 1519:13-29; Reeves et al. (2001) *Mol. Cell. Biol.* 21:575-594; Dolde et al. (2002) *Breast Cancer Research and Treatment* 71:181-191; Dhar et al. (2004) *Oncogene* 23:4466-4476; Takaha et al. (2004) *The Prostate* 60:160-167; Hommura et al. (2004) *Mol. Cancer Res.* 2:305-314; Xu et al. (2004) *Cancer Res.* 64:3371-3375; Tesfaye et al. (2007) *Cancer Res.* 67:3998-4004; Fusco and Fedele (2007) *Nat. Rev. Cancer* 7:899-910; Di Cello et al. (2008) *Molecular Cancer Therapeutics* 7:2090-2095; Hillion et al. (2008) *Cancer Res.* 68:10121-10127; Hillion et al. (2009) *Mol. Cancer Res.* 7:1803-1812; Hristov et al. (2010) *Mod. Pathol.* 23: 98-104; Reeves (2010) *Biochim. Biophys. Acta* 1799:3-14; Di Cello et al. (2013) *Leuk. Lymphoma* 54:1762-1768; Williams et al. (2013) *Anal. Bioanal. Chem.* 405:5013-5030; Pomeroy et al. (2002) *Nature* 415: 436-442; Flohr et al. (2003) *Histol. Histopathol.* 18: 999-1004; Shah et al. (2012) *PLoS One* 7: e48533).

The HMGA1 gene encodes the HMGA1a and HMGA1b chromatin remodeling proteins, which result from alternatively spliced messenger RNA (Resar (2010) *Cancer Research* 70:436-439; Reeves and Beckerbauer (2001) *Biochim. Biophys. Acta* 1519:13-29; Fusco and Fedele (2007) *Nat. Rev. Cancer* 7:899-910; Reeves (2010) *Biochim. Biophys. Acta* 1799:3-14). These low molecular weight (thus high mobility group) protein isoforms bind to the minor groove of chromatin at AT-rich regions. HMGA1 proteins modulate gene expression by altering chromatin structure and orchestrating the assembly of transcription factor complexes to enhanceosomes within enhancer or promoter regions throughout the genome. These proteins are highly expressed during embryogenesis with low or absent levels in adult tissues.

HMGA1 is overexpressed in all aggressive cancers studied to date, and high levels portend a poor prognosis in diverse tumors (Ben-Porath et al. (2008) *Nat. Genet.* 40:499-507; Resar (2010) *Cancer Research* 70:436-439; Chou et al. (2011) *Cell Res.* 21:518-529; Zhou et al. (2001) *Proc. Natl. Acad. Sci. USA* 98:13966-13971; Karp et al. (2011) *Blood* 117:3302-3310; Nelson et al. (2011) *Leuk Lymphoma* 52:1999-2006; Schuldenfrei et al. (2011) *BMC Genomics* 12:549; Belton et al. (2012) *PloS One* 7:e30034; Shah and Resar (2012) *Histol. Histopathol.* 27:567-579; Wood et al. (2000) *Mol. Cell. Biol.* 20:5490-5502; Pedulla et al. (2001) *Gene* 271:51-58; Reeves and Beckerbauer (2001) *Biochim. Biophys. Acta* 1519:13-29; Reeves et al. (2001) *Mol. Cell. Biol.* 21:575-594; Dolde et al. (2002) *Breast Cancer Research and Treatment* 71:181-191; Dhar et al. (2004) *Oncogene* 23:4466-4476; Takaha et al. (2004) *The Prostate* 60:160-167; Hommura et al. (2004) *Mol. Cancer Res.* 2:305-314; Xu et al. (2004) *Cancer Res.* 64:3371-3375;

Tesfaye et al. (2007) *Cancer Res.* 67:3998-4004; Fusco and Fedele (2007) *Nat. Rev. Cancer* 7:899-910; Di Cello et al. (2008) *Molecular Cancer Therapeutics* 7:2090-2095; Hillion et al. (2008) *Cancer Res.* 68:10121-10127; Hillion et al. (2009) *Mol. Cancer Res.* 7:1803-1812; Hristov et al. (2010) *Mod. Pathol.* 23: 98-104; Reeves (2010) *Biochim. Biophys. Acta* 1799:3-14; Di Cello et al. (2013) *Leuk. Lymphoma* 54:1762-1768; Williams et al. (2013) *Anal. Bioanal. Chem.* 405:5013-5030; Pomeroy et al. (2002) *Nature* 415: 436-442; Flohr et al. (2003) *Histol. Histopathol.* 18: 999-1004). In fact, HMGA1 proteins are the most abundant nonhistone chromatin binding proteins found in cancer cells. A recent landmark paper demonstrated that HMGA1 is essential for the cellular reprogramming of somatic cells to induced pluripotent stem cells by the four Yamanaka factors (Oct4, Sox2, Klf4, cMyc) (Shah et al. (2012) *PLoS One* 7: e48533). HMGA1 induces expression of key stem cell transcriptional networks in normal embryonic stem cells and during cellular reprogramming. The presently disclosed subject matter relates in part to the discovery that HMGA1 is a central factor in reprogramming cancer stem cells. In particular, it was discovered that the HMGA1 gene drives metastatic progression in triple-negative breast cancer cells (MDA-MB-231, Hs578T) by reprogramming cancer cells to a stem-like state. Silencing HMGA1 expression in invasive, aggressive breast cancer cells dramatically halted cell growth and resulted in striking morphologic changes from mesenchymal-like, spindle-shaped cells to cuboidal, epithelial-like cells. Mesenchymal genes (Vimentin, Twist) were repressed, while E-cadherin was induced in knock-down cells. Silencing HMGA1 also blocked oncogenic properties, including proliferation, migration, invasion, and orthotopic tumorigenesis. Metastatic progression following mammary implantation was almost completely abrogated in the HMGA1 knock-down cells. Moreover, silencing HMGA1 inhibited the stem cell properties and depleted breast cancer initiator/cancer stem cells. An HMGA1 signature in triple-negative breast cancer cells was also discovered that was highly enriched in embryonic stem cells. Accordingly, in some embodiments, the presently disclosed subject matter provides methods for inhibiting cancer stem cells and growth of aggressive and/or poorly differentiated metastatic tumors, by inhibiting the expression of the high mobility group A1 (HMGA1) gene.

I. Methods of Inhibiting Cancer Stem Cells

It has been found that silencing HMGA1 reprograms aggressive stem-like cancer cells into non stem-like cells with slow growth and altered properties. Accordingly, in some embodiments, the presently disclosed subject matter provides a method of inhibiting at least one cancer stem cell, the method comprising contacting at least one cancer stem cell with an effective amount of at least one HMGA1 inhibitor. Cancer stem cells (CSCs) are cancer cells that possess characteristics associated with normal stem cells, specifically the ability to differentiate into multiple cell types. CSCs may generate tumors through the stem cell processes of self-renewal and differentiation and are proposed to persist in tumors as a distinct population. In addition, they appear to be highly drug-resistant cells.

As used herein, an HMGA1 inhibitor is an agent that inhibits target gene expression (i.e., HMGA1 gene expression). As used herein, "inhibition of target gene expression" includes any decrease in expression or protein activity or level of the target gene (HMGA1 gene) or protein encoded by the target gene (HMGA1 protein). The decrease may be of at least 10%, 20%, 30%, 40%, 50%, 60%, 70%, 80%, 90%, 95% or 99% or more as compared to the expression of a target gene or the activity or level of the protein encoded by a target gene which has not been targeted by an RNA interfering agent. Certain exemplary methods of assaying for HMGA1 gene expression or HMGA1 protein activity include, but are not limited to, those methods disclosed herein as well as assays known to those skilled in the art (see, e.g., Liau et al. (2006) *Cancer Res.* 66:11613-11622; Liu et al. (2012) *Biotechnol. Appl. Biochem.* 59:1-5).

HMGA1 inhibitors for use in the presently disclosed methods include RNA interfering agents. An "RNA interfering agent" as used herein, is defined as any agent which interferes with or inhibits expression of a target gene, e.g., a marker of the presently disclosed subject matter, by RNA interference (RNAi). Such RNA interfering agents include, but are not limited to, nucleic acid molecules including RNA molecules which are homologous to the target gene, e.g., a marker of the presently disclosed subject matter, or a fragment thereof, short interfering RNA (siRNA), and small molecules which interfere with or inhibit expression of a target gene by RNA interference (RNAi). In some embodiments, at least one HMGA1 inhibitor is an RNA interfering agent.

"RNA interference (RNAi)" is an evolutionarily conserved process whereby the expression or introduction of RNA of a sequence that is identical or highly similar to a target gene results in the sequence specific degradation or specific post-transcriptional gene silencing (PTGS) of messenger RNA (mRNA) transcribed from that targeted gene (see Coburn & Cullen (2002) *J. Virol.* 76:9225), thereby inhibiting expression of the target gene (see, e.g., U.S. Patent Application Nos: 20030153519A1; 20030167490A1; and U.S. Pat. Nos. 6,506,559; 6,573,099). In one embodiment, the RNA is double stranded RNA (dsRNA). This process has been described in plants, invertebrates, and mammalian cells. In nature, RNAi is initiated by the dsRNA-specific endonuclease Dicer, which promotes processive cleavage of long dsRNA into double-stranded fragments termed siRNAs, siRNAs are incorporated into a protein complex that recognizes and cleaves target mRNAs. RNAi can also be initiated by introducing nucleic acid molecules, e.g., synthetic siRNAs or RNA interfering agents, to inhibit or silence the expression of target genes.

The presently disclosed subject matter also contemplates "short interfering RNA" (siRNA), also referred to herein as "small interfering RNA." Such a molecule is defined as an agent which functions to inhibit expression of a target gene, e.g., by RNAi. As used herein, the term siRNA is intended to be equivalent to any term in the art defined as a molecule capable of mediating sequence-specific RNAi. Such equivalents include, for example, double-stranded RNA (dsRNA), microRNA (mRNA), short hairpin RNA (shRNA), short interfering oligonucleotide, and post-transcriptional gene silencing RNA (ptgsRNA). An siRNA may be chemically synthesized, may be produced by in vitro transcription, or may be produced within a host cell. In one embodiment, siRNA is a double stranded RNA (dsRNA) molecule of about 15 to about 40 nucleotides in length, preferably about 15 to about 28 nucleotides, more preferably about 19 to about 25 nucleotides in length, and more preferably about 19, 20, 21, or 22 nucleotides in length, and may contain a 3' and/or 5' overhang on each strand having a length of about 0, 1, 2, 3, 4, or 5 nucleotides. The length of the overhang is independent between the two strands, i.e., the length of the overhang on one strand is not dependent on the length of the overhang on the second strand. Preferably the siRNA is capable of promoting RNA interference through degradation or specific post-transcriptional gene silencing (PTGS) of the target messenger RNA (mRNA).

In another embodiment, an siRNA is a small hairpin (also called stem loop) RNA (shRNA). In one embodiment, these shRNAs are composed of a short (e.g., 19-25 nucleotide) antisense strand, followed by a 5-9 nucleotide loop, and the analogous sense strand. Alternatively, the sense strand may precede the nucleotide loop structure and the antisense strand may follow. These shRNAs may be contained in plasmids, retroviruses, and lentiviruses and expressed from, for example, the pol III U6 promoter, or another promoter (see. e.g., Stewart et al. (2003) *RNA* 9:493-501). In a particular embodiment, the siRNA is an shRNA that targets the nucleotide sequence of SEQ ID NO:1 (see, e.g., Liau et al. (2006) *Cancer Res.* 66:11613-11622).

As used herein, inhibition of at least one cancer stem cell includes, but is not limited to, inhibition of oncogenic properties associated with both tumor initiation (orthotopic tumorigenesis) and tumor progression (migration, invasion, and metastatic progression), for example, inhibition of growth of cancer stem cells as compared to the growth of untreated or mock treated cells, inhibition of metastases, induction of cancer cell senescence, induction of cancer cell death, and reduction of tumor size.

As used herein, the term "contacting" means any action that results in at least one HMGA1 inhibitor of the presently disclosed subject matter physically contacting at least one cell, such as a cancer stem cell. It thus may comprise exposing the cell(s) to the HMGA1 inhibitor in an amount sufficient to result in contact of at least one HMGA1 inhibitor with at least one cell. The method can be practiced in vitro or ex vivo by introducing, and preferably mixing, the HMGA1 inhibitor and cells in a controlled environment, such as a culture dish or tube. The method can be practiced in vivo, in which case contacting means exposing at least one cell in a subject to at least one HMGA1 inhibitor of the presently disclosed subject matter, such as administering the HMGA1 inhibitor to a subject via any suitable route. According to the presently disclosed subject matter, contacting may comprise introducing, exposing, and the like, the HMGA1 inhibitor at a site distant to the cells to be contacted, and allowing the bodily functions of the subject, or natural (e.g., diffusion) or man-induced (e.g., swirling) movements of fluids to result in contact of the HMGA1 inhibitor and cell(s). In general, the term "effective amount" refers to the amount of an agent, such as an HMGA1 inhibitor, to elicit the desired biological response, such as inhibition of a cancer stem cell.

In addition, "a therapeutically effective amount," of a therapeutic agent refers to the amount of the agent necessary to elicit the desired biological response. As will be appreciated by those of ordinary skill in this art, the effective amount of an agent may vary depending on such factors as the desired biological endpoint, the agent to be delivered, the composition of the pharmaceutical composition, the target tissue or cell, and the like. More particularly, the term "effective amount" refers to an amount sufficient to produce the desired effect, e.g., to reduce or ameliorate the severity, duration, progression, or onset of a disease, disorder, or condition (e.g., aggressive and/or poorly differentiated metastatic cancer), or one or more symptoms thereof; prevent the advancement of a disease, disorder, or condition, cause the regression of a disease, disorder, or condition; prevent the recurrence, development, onset or progression of a symptom associated with a disease, disorder, or condition, or enhance or improve the prophylactic or therapeutic effect(s) of another therapy. Accordingly, as used herein, treatment of aggressive and/or poorly differentiated metastatic cancer, includes, but is not limited to, reduction in cancer growth or tumor burden, induction of cancer cell senescence, induction of apoptosis of cancer cells, induction of cancer cell death, inhibition of angiogenesis, enhancement of cancer cell apoptosis, and inhibition of metastases.

In some embodiments, inhibiting at least one cancer stem cell is selected from the group consisting of i) inhibiting proliferation of the at least one cancer stem cell; ii) inhibiting self-renewal of the at least one cancer stem cell; iii) inhibiting anchorage-independent growth of the at least one cancer stem cell; iv) inhibiting migration of the at least one cancer stem cell; v) inhibiting invasion of the at least one cancer stem cell; vi) reprogramming the at least one cancer stem cell from a stem-like state that is refractory to apoptosis to a non stem-like state that is susceptible to apoptosis; and vii) combinations thereof. As used herein, the term "proliferation" refers to an increase in the number of cells as a result of cell growth and cell division. Thus, inhibiting proliferation of a cancer stem cell means to reduce its ability to undergo cell growth and/or cell division. "Self-renewal" refers to the process by which stem cells divide to make more stem cells, thereby perpetuating the stem cell pool. Self-renewal is division with maintenance of the undifferentiated state. Some cancer arises from mutations that inappropriately activate self-renewal programs. "Migration" refers to the ability of a cell to move. "Invasion" refers to the ability of cells to become motile and to navigate through the extracellular matrix within a tissue or to infiltrate neighboring tissues. Cancer cells that become invasive may disseminate to secondary sites and form metastases. "Anchorage-independent growth" refers to the ability of a cell to have colony forming capacity in semisolid media, which is connected with tumor cell aggressiveness in vivo. "Reprogramming" a cell refers to causing a change in the cell, for example, by changing a cancer stem cell from a cell that is refractory or resistant to apoptosis (e.g., as a result of exposure to a chemotherapeutic agent) to a state where the cell is susceptible to apoptosis. As used herein, "apoptosis", also referred to as programmed cell death, refers to the process of cell self-destruction.

In some embodiments, at least one cancer stem cell is in an aggressive and/or poorly differentiated metastatic tumor, and inhibiting the at least one cancer stem cell inhibits at least one of: i) growth of the aggressive and/or poorly differentiated metastatic tumor; ii) proliferation of the aggressive and/or poorly differentiated metastatic tumor; iii) migration of the aggressive and/or poorly differentiated metastatic tumor; iv) invasion of the aggressive and/or poorly differentiated metastatic tumor; v) initiation of new aggressive and/or poorly differentiated metastatic tumors; and vi) combinations thereof. As used herein, the term "aggressive" in the context of a tumor/cancer means that the tumor/cancer exhibits rapid growth, is more likely to have spread by the time it has been diagnosed, and is more refractory than other non-aggressive forms of the tumor/cancer in that it is more likely to recur after treatment as compared to the non-aggressive form of the tumor/cancer. As used herein, the term "poorly differentiated" refers to a cell that is abnormal looking as compared to a normal cell. Poorly differentiated cells in a tumor are an indicator of a more aggressive tumor. A "metastatic tumor" or "metastatic cancer" is a tumor or cancer that has spread from the place where it first started to another place in the body.

HMGA1 is overexpressed in bulk tumor mass of aggressive and/or poorly differentiated metastatic cancers with the highest levels of HMGA1 overexpression occurring in the cancer stem cells of the aggressive and/or poorly differentiated metastatic cancer. Accordingly, in some embodiments, at least one cancer stem cell expresses greater levels of HMGA1 as compared to non-stem cancer cells in the aggressive and/or poorly differentiated metastatic tumor. In some embodiments, at least one cancer stem cell expresses greater levels of HMGA1 as compared to normal tissue or precursor lesions. In some embodiments, an aggressive and/or poorly differentiated metastatic tumor expresses greater levels of HMGA1 as compared to normal tissue or precursor lesions. As used herein, the term "greater levels" means a level of HMGA1 in a sample that is higher than the level of expression of HMGA1 in a control sample by at least 1.5 fold, 1.6 fold, 1.7 fold, 1.8 fold, 1.9 fold, 2.0 fold, 2.1 fold, 2.2 fold, 2.3 fold, 2.4 fold, 2.5 fold, 2.6 fold, 2.7 fold, 2.8 fold, 2.9 fold, 3.0 fold, 3.1 fold, 3.2 fold, 3.3 fold, 3.4 fold, 3.5 fold, 3.6 fold, 3.7 fold, 3.8 fold, 3.9 fold, 4.0 fold, 4.1 fold, 4.2 fold, 4.3 fold, 4.4 fold, 4.5 fold, 4.6 fold, 4.7 fold, 4.8 fold, 4.9 fold, 5.0 fold or more. In other embodiments, the term "greater levels" means a level of HMGA1 in a sample that is higher than the level of HMGA1 in a control sample by at least 10 fold, 20 fold, 50 fold, 100 fold, 200 fold, 300 fold, 400 fold or more.

A "cancer" in a patient refers to the presence of cells possessing characteristics typical of cancer-causing cells, for example, uncontrolled proliferation, loss of specialized functions, immortality, significant metastatic potential, significant increase in anti-apoptotic activity, rapid growth and proliferation rate, and certain characteristic morphology and cellular markers. In some circumstances, cancer cells will be in the form of a tumor; such cells may exist locally within an animal, or circulate in the blood stream as independent cells. Cancer as used herein includes newly diagnosed or recurrent cancers, including without limitation, blastomas, carcinomas, gliomas, leukemias, lymphomas, melanomas, myeloma, and sarcomas. Cancer as used herein includes, but is not limited to, head cancer, neck cancer, head and neck cancer, lung cancer, breast cancer, prostate cancer, colorectal cancer, esophageal cancer, stomach cancer, leukemia/lymphoma, uterine cancer, skin cancer, endocrine cancer, urinary cancer, pancreatic cancer, gastrointestinal cancer, ovarian cancer, cervical cancer, and adenomas. In some embodiments, the cancer comprises Stage 0 cancer. In some embodiments, the cancer comprises Stage I cancer. In some embodiments, the cancer comprises Stage II cancer. In some embodiments, the cancer comprises Stage III cancer. In some embodiments, the cancer comprises Stage IV cancer. In some embodiments, the cancer is refractory and/or metastatic. In some embodiments, at least one cancer stem cell is selected from the group consisting of a triple-negative breast cancer cell, a pancreatic ductal adenocarcinoma cell, a colorectal cancer cell, and a leukemia cell.

In some embodiments, at least one HMGA1 inhibitor reduces the expression level and/or activity of HMGA1. As used herein, the term "expression level" refers to the amount of a mRNA or protein detected. Levels can be detected at the transcriptional level, the translational level, and the post-translational level, for example. "mRNA expression levels" refers to the amount of mRNA detected in a sample and "protein expression levels" refers to the amount of protein detected in a sample.

In some embodiments, the methods further comprise contacting at least one cancer stem cell with a chemotherapeutic agent. A "chemotherapeutic agent" is used to connote a compound or composition that is administered in the treatment of cancer. Chemotherapeutic agents useful in methods, compositions, and kits disclosed herein include, but are not limited to, alkylating agents such as thiotepa, temozolomide, and cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamime; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU) folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytosine arabinoside, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenishers such as folinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK; razoxane; sizofuran; spirogermanium; tenuazonic acid; triaziquone; 2,2', 2"-trichlorotriethylamine; urethan; vindesine; dacarbazine; mannomustine; mitobronitol; mitolactol; pipobroman; gacytosine; arabinoside (Ara-C); taxoids, e.g. paclitaxel and docetaxel; chlorambucil; gemcitabine; 6-thioguanine; mercaptopurine; platinum analogs such as cisplatin and carboplatin; vinblastine; platinum; etoposide; ifosfamide; mitomycin C; mitoxantrone; vincristine; vinorelbine; navelbine; novantrone; teniposide; daunomycin; aminopterin; xeloda; ibandronate; CPT11; topoisomerase inhibitor RFS 2000; difluoromethylornithine; retinoic acid; esperamicins; capecitabine; immune system blockers, e.g. rapamycin; amino acid modifiers, e.g. asparaginase; and pharmaceutically acceptable salts, acids or derivatives of any of the above. Chemotherapeutic agents also include anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above.

In some embodiments, the chemotherapeutic agent is a topoisomerase inhibitor. Topoisomerase inhibitors are chemotherapy agents that interfere with the action of a topoisomerase enzyme (e.g., topoisomerase I or II). Topoisomerase inhibitors include, but are not limited to, doxorubicin HCl, daunorubicin citrate, mitoxantrone HCl, actinomycin D, etoposide, topotecan HCl, teniposide, and irinotecan, as well as pharmaceutically acceptable salts, acids, or derivatives of any of these.

In some embodiments, the chemotherapeutic agent is an anti-metabolite. An anti-metabolite is a chemical with a structure that is similar to a metabolite required for normal biochemical reactions, yet different enough to interfere with one or more normal functions of cells, such as cell division. Anti-metabolites include, but are not limited to, gemcitabine, fluorouracil, capecitabine, methotrexate sodium, ralitrexed, pemetrexed, tegafur, cytosine arabinoside, thioguanine, 5-azacytidine, 6-mercaptopurine, azathioprine, 6-thioguanine, pentostatin, fludarabine phosphate, and cladribine, as well as pharmaceutically acceptable salts, acids, or derivatives of any of these.

In certain embodiments, the chemotherapeutic agent is an antimitotic agent, including, but not limited to, agents that bind tubulin. In some embodiments, the agent is a taxane. In certain embodiments, the agent is paclitaxel or docetaxel, or a pharmaceutically acceptable salt, acid, or derivative of paclitaxel or docetaxel. In certain alternative embodiments, the antimitotic agent comprises a *vinca* alkaloid, such as vincristine, binblastine, vinorelbine, or vindesine, or pharmaceutically acceptable salts, acids, or derivatives thereof. In some embodiments, the chemotherapeutic agent is gemcitabine.

In some embodiments, at least one cancer stem cell is contacted in a subject. In some embodiments, the subject is a human subject.

II. Methods of Treating Aggressive and/or Poorly Differentiated Metastatic Cancer In some embodiments, an aggressive and/or poorly differentiated metastatic cancer cell may be contacted with an HMGA1 inhibitor within a subject, and such contact may result in treatment of aggressive and/or poorly differentiated metastatic cancer in the subject. In some embodiments, at least some of the cells from the aggressive and/or poorly differentiated metastatic cancer comprise cancer stem cells. Accordingly, the presently disclosed subject matter also provides methods of treating aggressive and/or poorly differentiated metastatic cancer in a subject in need thereof. In such embodiments, the methods include administering a therapeutically effective amount of at least one HMGA1 inhibitor to a subject in need thereof to treat aggressive and/or poorly differentiated metastatic cancer. In some embodiments, the aggressive and/or poorly differentiated metastatic cancer is selected from the group consisting of triple-negative breast cancer, pancreatic ductal adenocarcinoma cell, colorectal cancer cell, and leukemia. In some embodiments, the aggressive and/or poorly differentiated metastatic cancer comprises at least one cancer stem cell that overexpresses HMGA1 protein.

The presently disclosed methods may further comprise selecting the subject for treatment of the aggressive and/or poorly differentiated metastatic cancer with at least one HMGA1 inhibitor. In some embodiments, selecting the subject for treatment of the aggressive and/or poorly differentiated metastatic cancer comprises: (i) obtaining a biological sample comprising cells from the aggressive and/or poorly differentiated metastatic cancer; (ii) assaying the level of HMGA1 expression in the cells from the aggressive and/or poorly differentiated metastatic cancer; (iii) comparing the level of HMGA1 expression in the cells to the level of HMGA1 expression in a normal control cell; and (iv) selecting the subject for treatment of the aggressive and/or poorly differentiated metastatic cancer with the at least one HMGA1 inhibitor if the level of HMGA1 expression in the cells is greater than the level of HMGA1 expression in the normal control cell.

The terms "sample," "subject sample," "biological sample," and the like, encompass a variety of sample types obtained from a subject, individual, or subject and can be used in a diagnostic or monitoring assay. The subject sample may be obtained from a healthy subject, a diseased subject or a subject having associated symptoms of cancer. Moreover, a sample obtained from a subject can be divided and only a portion may be used for diagnosis. Further, the sample, or a portion thereof, can be stored under conditions to maintain sample for later analysis. The definition specifically encompasses blood and other liquid samples of biological origin (including, but not limited to, peripheral blood, serum, plasma, cerebrospinal fluid, urine, saliva, stool and synovial fluid), solid tissue samples such as a biopsy specimen or tissue cultures or cells derived therefrom and the progeny thereof. In a specific embodiment, a sample comprises a cancer tissue sample. The definition also includes samples that have been manipulated in any way after their procurement, such as by centrifugation, filtration, precipitation, dialysis, chromatography, treatment with reagents, washed, or enriched for certain cell populations. The terms further encompass a clinical sample, and also include cells in culture, cell supernatants, tissue samples, organs, and the like. Samples may also comprise fresh-frozen and/or formalin-fixed, paraffin-embedded tissue blocks, such as blocks prepared from clinical or pathological biopsies, prepared for pathological analysis or study by immunohistochemistry. In some embodiments, the biological sample is selected from the group consisting of a breast tissue sample, a pancreatic tissue sample, a colon tissue sample, and a bone marrow tissue sample.

In some embodiments, at least one HMGA1 inhibitor is formulated for delivery in a nanoparticle. As used herein, the term "nanoparticle," refers to a particle having at least one dimension in the range of about 1 nm to about 1000 nm, including any integer value between 1 nm and 1000 nm (including about 1, 2, 5, 10, 20, 50, 60, 70, 80, 90, 100, 200, 500, and 1000 nm and all integers and fractional integers in between).

As used herein, the term "subject" treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for the diagnosis or treatment of an existing disease, disorder, condition or the prophylactic diagnosis or treatment for preventing the onset of a disease, disorder, or condition or an animal subject for medical, veterinary purposes, or developmental purposes. Suitable animal subjects include mammals including, but not limited to, primates, e.g., humans, monkeys, apes, gibbons, chimpanzees, orangutans, macaques and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, guinea pigs, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a disease, disorder, or condition. Thus, the terms "subject" and "patient" are used interchangeably herein. Subjects also include animal disease models (e.g., rats or mice used in experiments, and the like).

As described herein, the presently disclosed HMGA1 inhibitor can be administered to a subject for therapy by any suitable route of administration, including orally, nasally, transmucosally, ocularly, rectally, intravaginally, parenterally, including intramuscular, subcutaneous, intramedullary injections, as well as intrathecal, direct intraventricular, intravenous, intra-articular, intra-sternal, intra-synovial, intra-hepatic, intralesional, intracranial, intraperitoneal, intranasal, or intraocular injections, intracisternally, topically, as by powders, ointments or drops (including eye-drops), including buccally and sublingually, transdermally, through an inhalation spray, or other modes of delivery known in the art.

The phrases "systemic administration," "administered systemically," "peripheral administration" and "administered peripherally" as used herein mean the administration of at least one HMGA1 inhibitor such that it enters the patient's system and, thus, is subject to metabolism and other like processes, for example, subcutaneous administration.

The phrases "parenteral administration" and "administered parenterally" as used herein mean modes of administration other than enteral and topical administration, usually by injection, and includes, without limitation, intravenous, intramuscular, intarterial, intrathecal, intracapsular, intraorbital, intraocular, intracardiac, intradermal, intraperitoneal, transtracheal, subcutaneous, subcuticular, intraarticular, subcapsular, subarachnoid, intraspinal and intrasternal injection and infusion.

Regardless of the route of administration selected, compositions comprising an HMGA1 inhibitor may be formulated into pharmaceutically acceptable dosage forms. One skilled in the art can select appropriate formulation components, such as carriers, buffers, adjuvants, etc., according to the route of administration and/or the subject being treated.

Actual dosage levels of an HMGA1 inhibitor can be varied so as to obtain an amount of the active ingredient that is effective to achieve the desired therapeutic response for a particular subject, composition, route of administration, and disease, disorder, or condition without being toxic to the subject. The selected dosage level will depend on a variety of factors including the activity of the particular composition employed, the route of administration, the time of administration, the rate of excretion of the particular composition being employed, the duration of the treatment, other drugs, and/or materials used in combination with the particular composition employed, the age, sex, weight, condition, general health and prior medical history of the patient being treated, and like factors well known in the medical arts. Accordingly, a physician having ordinary skill in the art can readily determine and prescribe the effective amount of the presently disclosed composition required. Accordingly, the dosage range for administration will be adjusted by the physician as necessary, as described more fully elsewhere herein.

III. Methods of Selecting a Subject with Aggressive and/or Poorly Differentiated Metastatic Cancer In some embodiments, the presently disclosed method is a method of selecting a subject with an aggressive and/or poorly differentiated metastatic cancer for treatment with at least one HMGA1 inhibitor, the method comprising: (a) obtaining a biological sample from the subject, wherein the biological sample comprises cells from the aggressive and/or poorly differentiated metastatic cancer; (b) determining the level of expression of HMGA1 in the biological sample; (c) comparing the level of expression of HMGA1 in the biological sample with the level of expression of HMGA1 in a control sample; and (d) selecting the subject with aggressive and/or poorly differentiated metastatic cancer for treatment with at least one HMGA1 inhibitor when the level of HMGA1 expression in the biological sample is greater than the level of HMGA1 expression in the control sample.

IV. Methods of Diagnosing an Aggressive and/or Poorly Differentiated Metastatic Cancer The presently disclosed subject matter also provides methods of diagnosing an aggressive and/or poorly differentiated metastatic cancer in a subject in need thereof. In such embodiments, the methods comprise: (a) obtaining a biological sample from the subject, wherein the biological sample comprises cells suspected of being aggressive and/or poorly differentiated metastatic cancer cells; (b) determining the level of expression of two or more genes selected from Table I in the biological sample; and (c) comparing the level of expression of the two or more genes in the biological sample with the level of expression of the two or more genes in a control sample; wherein a significant difference in the level of expression of the two or more genes in the biological sample compared to the level of expression of the two or more genes in the control sample indicates that the biological sample comprises at least one aggressive and/or poorly differentiated metastatic cancer cell.

TABLE 1

Differentially Expressed Genes Induced By HMGA1

| Gene | Entrez Gene ID | Direction |
|---|---|---|
| SLC17A5 | 26503 | Down Expressed |
| PGRMC1 | 10857 | Down Expressed |
| TMCO1 | 54499 | Up Expressed |
| SLC9A6 | 10479 | Down Expressed |
| ARL2BP | 23568 | Down Expressed |
| DRAM2 | 128338 | Down Expressed |
| PLAT | 5327 | Down Expressed |
| SEPT2 | 4735 | Down Expressed |
| PSG4 | 5672 | Up Expressed |
| RPS10P7 | 376693 | Down Expressed |
| INPP5A | 3632 | Down Expressed |
| CAMK2N1 | 55450 | Down Expressed |
| OR6X1 | 390260 | Up Expressed |
| TGFBR2 | 7048 | Up Expressed |
| SLC37A2 | 219855 | Down Expressed |
| GRB2 | 2885 | Down Expressed |
| B3GALT5 | 10317 | Down Expressed |
| TAF9B | 51616 | Down Expressed |
| HIST1H4L | 8368 | Down Expressed |
| FOS | 2353 | Up Expressed |
| SRPX | 8406 | Down Expressed |
| LIPA | 3988 | Down Expressed |
| HMGA1 | 3159 | Down Expressed |
| CNDP2 | 55748 | Down Expressed |
| BOK | 666 | Down Expressed |
| ABCA1 | 19 | Down Expressed |
| MSRB3 | 253827 | Up Expressed |
| WSB2 | 55884 | Down Expressed |
| CLIP1 | 6249 | Down Expressed |
| WIPF1 | 7456 | Down Expressed |
| MYEOV | 26579 | Down Expressed |
| SLC26A2 | 1836 | Up Expressed |

TABLE 1-continued

Differentially Expressed Genes Induced By HMGA1

| Gene | Entrez Gene ID | Direction |
|---|---|---|
| WDFY1 | 57590 | Up Expressed |
| SYPL1 | 6856 | Down Expressed |
| STEAP3 | 55240 | Down Expressed |
| C5orf28 | 64417 | Up Expressed |
| IRAK2 | 3656 | Down Expressed |
| NFIB | 4781 | Up Expressed |
| LOC100134868 | 100134868 | Up Expressed |
| IPMK | 253430 | Down Expressed |
| ICK | 22858 | Down Expressed |
| PORCN | 64840 | Down Expressed |
| SFXN1 | 94081 | Up Expressed |
| APOL6 | 80830 | Down Expressed |
| C12orf49 | 79794 | Down Expressed |
| PIGO | 84720 | Down Expressed |
| AKAP6 | 9472 | Up Expressed |
| ULBP3 | 79465 | Down Expressed |
| GPR45 | 11250 | Down Expressed |
| RACGAP1 | 29127 | Down Expressed |
| MT1E | 4493 | Down Expressed |
| C3orf34 | 84984 | Up Expressed |
| STX19 | 415117 | Down Expressed |
| GRAMD3 | 65983 | Up Expressed |
| SLC1A3 | 6507 | Up Expressed |
| HMGCS1 | 3157 | Up Expressed |
| SEC24D | 9871 | Up Expressed |
| MAP3K13 | 9175 | Down Expressed |
| GPR110 | 266977 | Down Expressed |
| TSPAN11 | 441631 | Down Expressed |
| OR6F1 | 343169 | Down Expressed |
| PLAU | 5328 | Down Expressed |
| ALDH1A3 | 220 | Down Expressed |

As used herein, the term "biomarker" refers to any gene, RNA or protein whose level of expression in a cell or tissue is altered in some way compared to that of a normal or healthy cell or tissue. Biomarkers of the presently disclosed subject matter are selective for an aggressive and/or poorly differentiated metastatic cancer and comprise two or more genes comprising embryonic development genes, tissue development genes, cellular development genes, cell death and survival genes, cell movement genes, or a combination thereof. In particular, biomarkers of the presently disclosed subject matter that are selective for aggressive and/or poorly differentiated metastatic cancer include 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62 or 63 genes selected from Table I in the biological sample.

In some embodiments, the significant difference in expression of two or more genes in the biological sample compared to the control sample comprises increased expression of TMCO1, PSG4, OR6X1, TGFBR2, FOS, MSRB3, SLC26A2, WDFY1, C5orf28, NFIB, LOC100134868, SFXN1, AKAP6, C3orf34, GRAMD3, SLC1A3, HMGCS1, and/or SEC24D in the biological sample.

In some embodiments, the significant difference in expression of two or more genes in the biological sample compared to the control sample comprises decreased expression of SLC17A5, PGRAMC1, SLC9A6, ARL2BP, DRAM2, PLAT, SEPT2, RPS10P7, INPP5A, CAMK2N1, SLC37A2, GRB2, B3GALT5, TAF9B, HIST1H4L, SRPX, LIPA, HMGA1, CNDP2, BOK, ABCA1, WSB2, CLIP1, WIPF1, MMYEOV, SYPL1, STEAP3, IRAK2, IPMK, ICK, PORCN, APOL6, C12orf49, PIGO, ULBP3, GPR45, RACGAP1, MT1E, STX19, MAP3K13, GPR110, TSPAN11, OR6F, PLAU, and/or ALDH1A3 in the biological sample.

In another embodiment, the significant difference in expression of two or more genes in the biological sample compared to the control sample comprises increased expression of TGFβ1, FOS, cMYC, STAT3, and/or TMCO1 in the biological sample and/or decreased expression of ARL2BP, PGRMC1, and/or GRB2 in the biological sample.

As used herein, the term "level of expression" of a biomarker refers to the amount of biomarker detected. Levels of biomarker can be detected at the transcriptional level, the translational level, and the post-translational level, for example. As used herein, the term "diagnosing" refers to the process of attempting to determine or identify a disease or disorder.

As used herein, the term "comparing" refers to making an assessment of how the proportion or level of one or more biomarkers in a sample from a subject relates to the proportion or level of the corresponding one or more biomarkers in a standard or control sample. For example, "comparing" may refer to assessing whether the proportion or level of one or more biomarkers in a sample from a subject is the same as, more or less than, or different from the proportion or level of the corresponding one or more biomarkers in a standard or control sample. More specifically, the term may refer to assessing whether the proportion or level of one or more biomarkers in a sample from a subject is the same as, more or less than, different from or otherwise corresponds (or not) to the proportion or level of predefined biomarker levels that correspond to, for example, a subject having an aggressive and/or poorly differentiated metastatic cancer. In a specific embodiment, the term "comparing" refers to assessing whether the level of one or more biomarkers of the presently disclosed subject matter in a sample from a subject is the same as, more or less than, different from or otherwise correspond (or not) to levels of the same biomarkers in a control sample (e.g., predefined levels that correlate to individuals without an aggressive and/or poorly differentiated metastatic cancer, standard biomarker levels, and the like).

As used herein, the terms "indicates" or "correlates" (or "indicating" or "correlating," or "indication" or "correlation," depending on the context) in reference to a parameter, e.g., a modulated proportion or level in a sample from a subject, may mean that the subject has an aggressive and/or poorly differentiated metastatic cancer. In specific embodiments, the parameter may comprise the level of one or more biomarkers of the presently disclosed subject matter. A particular set or pattern of the amounts of one or more biomarkers may indicate that a subject has an aggressive and/or poorly differentiated metastatic cancer. In other embodiments, a particular set or pattern of the amounts of one or more biomarkers may be correlated to a subject being unaffected (i.e., indicates a subject does not have an aggressive and/or poorly differentiated metastatic cancer). In certain embodiments, "indicating," or "correlating," as used according to the presently disclosed subject matter, may be by any linear or non-linear method of quantifying the relationship between levels of biomarkers to a standard, control or comparative value for the assessment of the diagnosis, prediction of an aggressive and/or poorly differentiated metastatic cancer, assessment of efficacy of clinical treatment, identification of a subject that may respond to a particular treatment regime or pharmaceutical agent, monitoring of the progress of treatment, and in the context of a screening assay, for the identification of a therapeutic to treat an aggressive and/or poorly differentiated metastatic cancer.

A "subject" can include a subject afflicted with or suspected of being afflicted with a condition or disease. The subject may have mild, intermediate or severe disease. The subject may be treatment naive, responding to any form of treatment, or refractory. The subject may be an individual in need of treatment or in need of diagnosis based on particular symptoms or family history.

As used herein, the term "subject at risk" of getting a disease refers to estimating that a subject will have a disease or disorder in the future based on the subject's current symptoms, family history, lifestyle choices, and the like.

As used herein, the term "disease" refers to any condition, dysfunction or disorder that damages or interferes with the normal function of a cell, tissue, or organ.

The terms "measuring" and "determining" are used interchangeably throughout, and refer to methods which include obtaining a subject sample and/or detecting the level of a biomarker(s) in a sample. In one embodiment, the terms refer to obtaining a subject sample and detecting the level of one or more biomarkers in the sample. In another embodiment, the terms "measuring" and "determining" mean detecting the level of one or more biomarkers in a subject sample. Measuring can be accomplished by methods known in the art and those further described herein. The term "measuring" is also used interchangeably throughout with the term "detecting."

Various methodologies of the presently disclosed subject matter include a step that involves comparing a value, level, feature, characteristic, property, and the like, to a "suitable control," referred to interchangeably herein as an "appropriate control" or a "control sample." A "suitable control," "appropriate control" or a "control sample" is any control or standard familiar to one of ordinary skill in the art useful for comparison purposes. In one embodiment, a "suitable control" or "appropriate control" is a value, level, feature, characteristic, property, and the like, determined in a cell, organ, or subject, e.g., a control or normal cell, organ, or subject, exhibiting, for example, normal traits. For example, the biomarkers of the presently disclosed subject matter may be assayed for levels in a sample from an unaffected individual (UI) or a normal control individual (NC) (both terms are used interchangeably herein). In another embodiment, a "suitable control" or "appropriate control" is a value, level, feature, characteristic, property, and the like, determined prior to performing a therapy (e.g., a cancer treatment) on a subject. In yet another embodiment, a transcription rate, mRNA level, translation rate, protein level, biological activity, cellular characteristic or property, genotype, phenotype, and the like, can be determined prior to, during, or after administering a therapy into a cell, organ, or subject. In a further embodiment, a "suitable control" or "appropriate control" is a predefined value, level, feature, characteristic, property, and the like. A "suitable control" can be a profile or pattern of levels of one or more biomarkers of the presently disclosed subject matter that correlates to the presence of an aggressive and/or poorly differentiated metastatic cancer, to which a subject sample can be compared. The subject sample can also be compared to a negative control, i.e., a profile that correlates to not having an aggressive and/or poorly differentiated metastatic cancer.

V. General Definitions

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%6, in some embodiments ⅙, in some embodiments ±0.5%6, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

Methods
Ethics Statement:
All animal experiments were conducted in accordance with a protocol approved by the Johns Hopkins University Animal Care and Use Committee (protocol #MO11M270). Mice were housed in a sterile environment where they had free access to food and water as outlined in the institutional guidelines.

Cell Culture and Proliferation Assay:

Cells (MDA-MB-231 and Hs578T) were cultured as recommended (ATCC). For proliferation assays, cells were seeded (7,500/well) and counted using an automated cell counter (Nexcelom). Each experiment was done in triplicate and performed at least twice.

RNA Interference:

The short-hairpin RNA interference vector for HMGA1 targets 5'-CAACTCCAGGAAGGAAACCAA-3' (SEQ ID NO: 1) and has been described elsewhere (Liau et al. (2006) Cancer Res. 66:11613-11622). Virus was prepared as previously described. The empty vector was used as a negative control as described (Belton et al. (2012) PloS One 7:e30034). Polyclonal, transduced cells were selected and maintained in puromycin (1 ug/ml). To ensure that the effects of silencing HMGA were not a result of a single clone, independent, polyclonal transductions were done at least twice for each experiment. All functional experiments were performed in duplicate or triplicate and replicated after a repeat transduction experiment and polyclonal selection of shRNA or control cells. Repression of HMGA1 was confirmed in each case at the level of gene expression (qRT-PCR) and Western analysis.

Migration and Invasion Assays:

Invasion assays were performed as previously described (Hillion et al. (2009) Mol. Cancer Res. 7:1803-1812) with the following modifications. Briefly, 15,000 cells were resuspended in serum-free media (500 ul) and placed in the upper chamber of a 24-well BD BioCoat™ Matrigel™ Invasion Chamber coated with Matrigel. Invasion was calculated as the percentage of total cells that invaded into the bottom chamber containing complete media with serum. Migration was performed similarly, except that Matrigel was omitted.

Orthotopic Tumorigenicity and Metastatic Foci Experiments:

Cells (suspended in 75 ul phosphate-buffered saline (PBS)) were implanted into murine (NOD-scid IL2Rgamma$^{null}$) mammary fat pads with an equal volume of Matrigel. Tumor volumes (calculated by $4/3\pi \times length/2 \times width/2 \times depth/2$) were monitored daily until they reached 1-1.5 cm$^3$, after which mice were euthanized. The presence of tumor foci within the lung was analyzed histopathologically. For tail vein injection experiments, cells (10$^6$) were resuspended in PBS (150 ul). Mice were euthanized after 3 weeks, and lungs were examined histopathologically.

Mammosphere Assay:

Mammosphere assays were performed as previously described (Shaw et al. (2012) J. Mammary Gland Biol. Neoplasia 17: 111-117) and spheres (>50 um) were counted.

Western Analysis:

Western blots were performed as previously described (Belton et al. (2012) PloS One 7:e30034; Wood et al. (2000) Mol. Cell. Biol. 20:5490-5502), using commercial antibodies to HMGA1 (Abcam) and β-Actin (Cell Signaling), both at a 1:1000 dilution.

Gene Expression Analysis with Quantitative, Reverse Transcription PCR:

Total RNA was isolated using the Direct-zol RNA Mini-Prep kit (Zymo) and analyzed by qRT-PCR as previously described. The expression level of each gene was normalized to the human RPLP0 (Applied Biosystems) or β-actin gene. Primers for ECadherin, Snail, and Vimentin were previously described (Belton et al. (2012) PloS One 7:e30034; Mani et al. (2008) Cell 133:704-715).

HMGA1 Knock-Down and Gene Expression Profile Analysis:

HMGA1 was knocked-down in MDA-MB-231 cells using siRNA as previously described (Belton et al. (2012) PloS One 7:e30034; Tesfaye et al. (2007) Cancer Res. 67:3998-4004; Hillion et al. (2009)Mol. Cancer Res. 7:1803-1812). RNA was isolated and hybridized to the Affymetrix exon array (GeneChip Human Exon 1.0 ST Array) as previously described. Expression data was preprocessed using the robust microarray (RMA) algorithm (Irizarry et al. (2003) Nucleic Acids Res. 31: e15), as implemented in the oligo software package (Carvalho and Irizarry (2010) Bioinformatics 26: 2363-2367) available from Bioconductor (Gentleman et al. (2004) Genome Biol. 5: R80) and annotated to the most recent human genome using the getNetAffx function in the oligo package. Microarray data were uploaded to Gene Expression Omnibus (GSE45483). Expression profiles from HMGA1 knock-down cells were compared to control cells treated with the vector RNA using Bayes modified t-tests and the limma package from Bioconductor (Smyth (2005) "Bioinformatics and Computational Biology Solutions using R and Bioconductor". Springer-Verlag: 397-420). The analysis was focused on the 100 most differentially expressed transcripts.

To compare this signature to genes expressed in a panel of embryonic stem cells, induced pluripotent stem cells, embryoid bodies, and fibroblasts, expression profiles were downloaded for a 43 sample study (GSE25970) (Bock et al. (2011) Cell 44: 439-452) from the Gene Expression Omnibus (Barrett et al. (2005) Nucleic Acids Res. 33: D562-D566). Unsupervised cluster analysis was performed on all probes annotated to the 63 genes in the HMGA1 panel using agglomerative clustering with complete linkage. Euclidean distance and t-tests were used to compare probe-specific expression in stem cells and fibroblasts.

Pathway analysis of differentially expressed genes was performed using Ingenuity Pathway Analysis (IPA, Ingenuity Systems) as described (Schuldenfrei et al. (2011) BMC Genomics 12:549). IPA scores were generated for each network and indicate the likelihood that the focus genes present in the network could occur by chance alone. A score of ≥3 is considered significant because it represents a 1/1,000 chance that the network contains specific focus genes by random chance alone (Schuldenfrei et al. (2011) BMC Genomics 12:549).

Results

Silencing HMGA1 Halts Cell Proliferation and Reprograms Invasive, Mesenchymal-Like Cells:

To define the role of HMGA1 in oncogenic properties and tumor progression, HMGA1 expression was silenced using lentiviral-mediated delivery of short hairpin RNA (shRNA) ((Shah et al. (2012) PLoS One 7: e48533) in cell lines derived from aggressive, triple-negative breast cancers (MDAMB-231, Hs578T; FIG. 1A). Control cells were transduced with a control lentiviral vector (Belton et al. (2012) PloS One 7:e30034; Shah et al. (2012) PLoS One 7: e48533). It was discovered that cell proliferation was rapidly halted in both cell lines (FIG. 1B) within the first 4 days. Surprisingly, there was a dramatic change in cell morphology whereby the spindle-shaped, fibroblast-like cells became cuboidal and epithelial-like in appearance (FIG. 1C). Because these morphologic changes are consistent with a mesenchymal-epithelial transition, the expression of genes involved in a mesenchymal-epithelial transition was investigated (Belton et al. (2012) *PloS One* 7:e30034; Mani et al. (2008) *Cell* 133:704-715). In MDA-MB-231 cells, it was found that silencing HMGA1 led to a significant repression in the mesenchymal genes, Snail and Vimentin, while there was an increase in the gene expressing the epithelial marker, E-Cadherin (FIG. 1D). Similarly, in Hs578T cells, E-Cadherin was induced when HMGA1 was silenced. Tumor progression properties, including invasion and migration, were also assessed. In both cell lines, there was a marked reduction in migration and invasion in cells with silencing of HMGA141 (FIG. 1E). Together, these findings indicate that silencing HMGA1 results in a profound decrease in proliferation, migration, and invasion, as well as morphologic and gene expression changes consistent with a mesenchymal-epithelial transition.

Silencing HMGA1 Interferes with Orthotopic Tumorigenicity and Metastatic Progression:

Next, the role of HMGA1 on tumorigenesis was assessed using in vivo models of triple-negative breast cancer. First, tumor growth was assessed following mammary fat pad implantation. It was found that silencing HMGA1 in the aggressive MDA-MB-231 cells leads to a dramatic decrease in tumor growth following mammary fat pad implantation (FIG. 2A). Specifically, cells ($10^5$) transduced with control virus reached a volume of 0.53 $cm^3$±0.34 at 8 weeks following mammary fat pad implantation. In contrast, the tumors from cells transduced with HMGA1 shRNA (shHMGA1) were significantly smaller at 8 weeks following implantation (0.037 $cm^3$±0.058; p=0.016). Because there was a dramatic effect on primary tumorigenesis, it was also determined if silencing HMGA1 interferes with metastatic progression. Therefore, the lungs were evaluated histopathologically for tumor foci after necropsy. Strikingly, almost no metastatic lesions to the lungs in the mice implanted with the shHMGA1 cells were discovered as compared to the mice implanted with control cells in which there were extensive, coalescing sheets of metastatic tumor cells throughout the lungs following mammary implantation with $10^5$ cells (FIG. 2B). Metastatic progression was also assessed following mammary fat pad implantation with a greater number of cells ($10^7$) from a repeat transduction experiment, and sacrificed the mice after 5 weeks. With the higher number of cells, tumors formed from all injections (3/3 in controls and 3/3 in shHMGA1 cells (FIG. 2C). Although tumors were slightly smaller from the shHMGA1 cells, the difference was not significant (0.64±0.27 in controls versus 0.17±0.072 in shHMGA1 cells, p=0.08). Despite the similar tumor volumes, a dramatic decrease (>100-fold) was observed in metastatic foci in the shHMGA1 cells as compared to controls (0.67±1.15 versus >100 in all controls; p=0.00004; FIGS. 2C-2D). Lung foci was also assessed following tail vein injection of control or shHMGA1 cells ($10^6$) after 3 weeks. Only one lung focus was observed after injection of the shHMGA1 cells, while there were numerous foci in the control cells (0.25±0.5 versus 99.3±15.0; p=0.007; FIG. 5).

Silencing HMGA1 Blocks Mammosphere Formation and Depletes Tumor-Initiator Cells:

Because silencing HMGA1 has profound effects on oncogenic properties in vitro, primary tumorigenesis and metastatic progression in vivo, and expression of genes involved in epithelialmesenchymal transition, it was sought to determine its role in cancer stem cell characteristics. To this end, the epithelial stem cell property of mammosphere formation (Shaw et al. (2012) *J. Mammary Gland Biol. Neoplasia* 17: 111-117) was explored in the control and shHMGA1-treated cells (FIGS. 3A-3B). It was found that growth of primary, secondary, and tertiary mammospheres was significantly impaired in the MDA-MB-231 cells with silencing of HMGA1. Similarly, it was observed that there was a significant decrease in primary mammosphere formation in the Hs578T cells treated with shHMGA1. (Secondary or tertiary mammospheres do not form in control Hs578T cells, precluding analysis of these phenotypes). Next, orthotopic implantations were performed and tumorigenicity was assessed with limiting dilutions. As presented above, tumors formed in both control and shHMGA1 cells when $10^7$ or $10^5$ cells were implanted. In contrast, no tumors formed in the MDA-MB-231 cells with silencing of HMGA1 when $10^4$ cells were injected (0/3), while tumors formed in all control injections (3/3; FIG. 3C). These results indicate that silencing HMGA1 in MDA-MB-231 cells depletes the tumor-initiator or cancer stemlike cells and further underscores the role of HMGA4 as a key regulator of stem cell properties in aggressive, triple-negative breast cancer cells.

HMGA1 Induces a Stem Cell Signature in Triple-Negative Breast Cancer Cells:

To globally define the transcriptional networks regulated by HMGA1, gene expression profile analysis was performed in MDAMB-231 cells with or without HMGA1 knockdown. To this end, siRNA was used (Tesfaye et al. (2007) *Cancer Res.* 67:3998-4004; Hillion et al. (2009) *Mol. Cancer Res.* 7:1803-1812) and a rapid and significant reduction in HMGA1 expression was observed (FIG. 6A). HMGA1 mRNA falls dramatically by 48 hours, with persistent decreases at 72 hours (FIG. 6A). There was also a marked decrease in HMGA1 protein at 48 and 72 hours (FIG. 6B). Therefore, global gene expression profile analysis was performed at 48 hours using an Affymetrix exon array (GeneChip Human Exon 1.0 ST Array) with RNA from three independent replicates of each experimental condition. To define an HMGA1 signature in breast cancer, 100 transcripts that were most differentially expressed were identified. These 100 transcripts correspond to 63 unique genes. Because HMGA1 is enriched in embryonic stem cells and functional studies showed that it is required for cancer stem cell properties, the HMGA1 signature of 63 genes was compared to gene expression profiles from diverse pluripotent stem cells and differentiated cells, including embryonic stem cells (ESCs), induced pluripotent stem cells, embryoid bodies, and fibroblasts (Bock et al. (2011) *Cell* 44: 439-452). As shown, un-supervised cluster analysis of these genes separates the samples by cell type with a clear distinction between pluripotent stem cells and differentiated cells. Moreover, the HMGA1 signature is highly enriched in pluripotent/embryonic stem cells (p<0.001; FIG. 4A). A subset of the HMGA1 signature genes was validated using quantitative RT-PCR, and differential expression similar to the microarray gene expression results was found in all cases (FIG. 6C). These findings suggest that HMGA1 drives tumor progression by inducing stem cell transcriptional networks.

To elucidate cellular pathways regulated by HMGA1 in breast cancer, the HMGA1 signature was analyzed with Ingenuity Pathway Analysis (IPA, Ingenuity Systems). From the top list of differentially regulated genes, two pathways had significant network scores (69 and 46, respectively; FIGS. 4B and 7). The highest scoring network was embryonic development, tissue development, and cellular development. The top molecular and cellular functions were cell death and survival and cellular movement, while the top physiologic system development and functions included: 1. nervous system development and function, 2. organ morphology, and 3. embryonic development. In this network, the most down-regulated molecule was ARL2BP or ADP-ribosylation factor (ARF)-like 2 binding protein. This protein is a member of a functionally distinct group of RAS-related GTPases, called the ARF family. ARL2BP protein binds to ARL2.GTP with high affinity and plays a role in the nuclear translocation, retention and transcriptional activity of STAT3 (Muromoto et al. (2008) *Int. Immunol.* 20: 395-403). Notably, it was shown that HMGA1 induces STAT3 expression in lymphoid tumorigenesis, and STAT3 inhibitors are cytotoxic to the HMGA1-driven tumor cells (Hillion et al. (2008) *Cancer Res.* 68:10121-10127). TMCO1 or transmembrane and coiled-coil domains 1 protein was the most up-regulated protein in this network. Although its function is not known, it is associated with breast cancer cells [8882811 GEO Profiles-NCBI]. TGFβ1 is a major node and this protein is upregulated in diverse cancers and thought to promote invasion, migration, EMT and tumor progression (Massague (2008) *Cell* 134: 215-230). EGFR and MAPK are other important nodes that are activated in cancer and mediate proliferative signals (Schuldenfrei et al. (2011) *BMC Genomics* 12:549). Another central node was HIF-1 alpha, a key factor involved in angiogenesis during tumor progression and vascular development during embryogenesis (Semenza (2012) *Oncogene* in press. In addition, Myc was identified as a major node and prior studies found that not only does cMYC induce HMGA1 expression (Wood et al. (2000) *Mol. Cell. Biol.* 20:5490-5502), but HMGA1 also directly up-regulates cMYC expression (Shah et al. (2012) *PLoS One* 7: e48533). Myc also has a well-defined role in breast (Thibodeaus et al. (2009) *Breast Cancer Res. Treat.* 116:281-294; Tront et al. (2010) *Cancer Res.* 70:9671-9681) and other diverse cancers (Dang (2012) *Cell* 2:304-307) as well as in embryonic stem cells (Dang (2012) *Cell* 2:304-307; Nie et al. (2012) *Cell* 151:68-79. Thus, this pathway analysis further confirms the important role for HMGA1 in regulating embryonic stem cell networks during tumor progression in breast cancer.

Discussion

The presently disclosed subject matter reports for the first time that silencing HMGA1 induces a rapid and dramatic reprogramming of highly proliferative, invasive, mesenchymal-like breast cancer cells to more differentiated, slowly growing, epithelial-like cells. It was found that knock-down of HMGA1 has profound effects on oncogenic properties associated with both tumor initiation (orthotopic tumorigenesis) and tumor progression (migration, invasion, and metastatic progression). In fact, the in vivo effects on metastatic progression were even more pronounced than the effects on primary tumorigenesis, thus highlighting the role of HMGA1 in tumor progression. The changes induced by silencing HMGA1 are among the most striking alterations reported to date with knockdown of HMGA1 or most other oncogenes for that matter, both in degree and rate of onset. The profound effects could be related to the presently disclosed efficient, viral-mediated delivery of shRNA to repress HMGA1. In addition, triple-negative breast cancer cells may be highly dependent upon HMGA1 and related pathways for their oncogenic properties. Indeed, a study from the Broad Institute at MIT identified HMGA1 as a key transcription factor enriched in triple-negative breast cancer (Ben-Porath et al. (2008) *Nat. Genet.* 40:499-507). Moreover, expression of HMGA1 and 8 additional genes predicted poor outcomes in breast cancer, as well as brain and bladder cancer. Prior studies using antisense or dominant-negative approaches in triple-negative breast cancer cells (MDA-MB-231 or Hs578T) also showed that anchorage-independent cell growth or colony formation are inhibited by HMGA1 repression (Reeves et al. (2001) *Mol. Cell. Biol.* 21:575-594; Dolde et al. (2002) *Breast Cancer Research and Treatment* 71:181-191). There is also preliminary evidence demonstrating that HMGA1 expression correlates with more advanced nuclear grade in primary tumors (Asch & Resar, unpublished data).

Emerging evidence further indicates that HMGA1 is important in maintaining a de-differentiated, pluripotent stem-like state ((Shah et al. (2012) *PLoS One* 7: e48533). A recent landmark paper demonstrated that HMGA1 is required for cellular reprogramming of somatic cells to induced pluripotent stem cells (iPSCs) by the Yamanaka factors (Flohr et al. (2003) *Histol. Histopathol.* 18: 999-1004). Blocking HMGA1 expression or function prevents the derivation of iPSCs. In normal embryonic stem cells in culture and during the reprogramming process to iPSCs, HMGA1 activates expression of stem cell transcriptional networks. Recent studies also found that tumor progression and an epithelial-mesenchymal transition (EMT) involves transcriptional networks important in stem cells (Ben-Porath et al. (2008) *Nat. Genet.* 40:499-507; Schuldenfrei et al. (2011) *BMC Genomics* 12:549; Belton et al. (2012) *PloS One* 7:e30034; Shah et al. (2012) *PLoS One* 7: e48533; Mani et al. (2008) *Cell* 133:704-715). The first evidence linking HMGA1 to EMT came from an important study in 2001 in MCF-7 breast cancer cells, which demonstrated that forced expression of HMGA1 results in metastatic progression and histologic changes consistent with EMT in the epithelial MCF-7 breast cancer cell line (Dolde et al. (2002) *Breast Cancer Research and Treatment* 71:181-191). This group also found that HMGA1 induces changes in classes of genes involved in tumor progression. More recently, studies in colon cancer showed that HMGA1 is required for tumor progression and stem cell properties (Belton et al. (2012) *PloS One* 7:e30034). The presently disclosed subject matter shows that HMGA1 is required for mammosphere formation, including secondary and tertiary mammospheres in MDA-MB-231 cells. It has also been found that silencing HMGA1 depletes tumor initiator/cancer stem cells, indicating that targeting HMGA1 in breast cancer therapy could have an important impact on the cancer stem cell population, which is believed to be the basis for refractory disease in diverse tumors. These functional studies are corroborated by the HMGA1 signature and pathway analysis demonstrating that HMGA1 orchestrates transcriptional networks important in stem cells and metastatic progression.

There is a dire need to understand the molecular underpinnings of metastatic progression because this is the major cause of death in patients with cancer. Although cancer is a highly complex and heterogeneous disease, with significant heterogeneity even within a single tumor, increasing evidence indicates that common, central pathways exist that could serve as "Achilles heels" or rational therapeutic targets in diverse tumors. The presently disclosed subject matter underscores the fundamental role for HMGA1 in tumor progression in preclinical models for aggressive, triple-negative breast cancers and provides compelling evidence that HMGA1 is a master regulator in the evolution of primary tumors to metastatic disease.

Example 2

The HMGA1 gene encodes the HMGA1a and HMGA1b chromatin remodeling proteins, which regulate gene expression by altering chromatin structure. HMGA1 plays a central role in the development and progression of PDAC by acting as a master regulator of transcriptional networks that maintain tumor cells in a refractory, stem-like state (FIG. 8 and FIG. 9). It has been discovered that HMGA1 is overexpressed in >90% of PDACs with absent levels in precursor lesions and normal tissue. Moreover, previous work demonstrates that high levels of HMGA1 protein correlate positively with poor differentiation status and decreased survival. It was also found that HMGA1 is required for reprogramming somatic cells to induced pluripotent stem cells by the Yamanaka factors. In addition, it was discovered that HMGA1 induces stem cell transcriptional networks in cancer cells and normal stem cells. Taken together, these studies suggest that HMGA1 drives poor differentiation and metastatic progression in PDAC by inducing stem cell genes. Previous studies indicate that knock-down of HMGA1 blocks oncogenic phenotypes in vitro and metastatic progression in orthotopic murine models. Knock-down of HMGA1 also blocks cancer stem cell properties and depletes cancer stem cells/tumor initiator cells.

Results

Silencing HMGA1 with Short Hairpin RNA (shRNA) Reprograms PDAC Cells:

HMGA1 and HMGA2 expression levels in different pancreatic ductal adenocarcinoma cell (PDAC) lines are shown in FIG. 11. In low-passage PDAC cells derived from patient tumors (lines 10.7, 10.05) or MiaPaCa2 commercial PDAC cell lines, it was discovered that silencing HMGA1 using viral-mediated delivery of shRNA drastically impairs cell growth (FIG. 10 and FIG. 12). Surprisingly, there is also a dramatic change in morphology, with fibroblast-like cells becoming cuboidal or epithelial-like, consistent with a mesenchymal-epithelial transition, or MET (FIG. 11 and FIG. 14;) Preliminary studies also show that colony formation, migration, and invasion are disrupted in the HMGA1 knock-down cell. (FIG. 13 and FIG. 15B). In preliminary experiments, xenograft tumor formation was inhibited in the HMGA shRNA cells. Strikingly, it was also found that silencing HMGA1 blocks stem cell properties, including 3-dimensional (3-D) sphere formation in PDAC cells (FIG. 15C). HMGA knock-down also prevents tumor formation following injection of reduced numbers of cells or "limiting dilutions" in patient-derived PDAC cells; studies are underway to more precisely calculate the frequency of tumor-initiator cells in the control and wild type PDAC cells. This latter finding indicates that the tumor initiator/cancer stem cells (CSCs) are depleted in the HMGA1 knock-down cells. Similar findings were observed in other cancer cells treated with shRNA targeting HMGA1, including colorectal cancer (CRC) and leukemia cells (FIG. 16A. FIG. 16B and FIG. 16C). Tumorigenicity and additional oncogenic assays are underway in PDAC cells. Gene expression analysis is also planned to identify the molecular pathways that are disrupted after silencing HMGA1.

Systemic Nanoparticle (NP) Plasmid Delivery of shRNA to HMGA1:

The experiments shown herein demonstrate that silencing HMGA1 in PDAC cells is an effective anti-tumor therapy. Innovative NP platforms are being tested to systemically deliver shRNA plasmid DNA in vivo in preclinical animal models. It was found that there was a decrease in average tumor size in tumors treated with NP delivery of plasmid DNA vectors encoding shRNA to target HMGA1 as compared to control NPs (FIG. 17). On histologic examination, necrosis appeared to be increased in the tumors treated with the HMGA1-targeting vector (FIG. 18A and FIG. 18B). Fluorescent-activated cell sorting (FACS) analysis following injection of labeled DNA, however, showed that the plasmid was delivered to only ~5-30% of cells.

Discussion

Together, these results show that silencing HMGA1 reprograms aggressive stem-like cancer cells into non stem-like cells with slow growth and altered properties. Results demonstrated that silencing HMGA1 has dramatic effects on tumor cell appearance, proliferation and invasive properties. It was also found that silencing HMGA1 prevents 3D sphere formation and depletes cancer stem cells. Silencing HMGA1 also halts proliferation and blocks hallmarks of aggressive PDA including self-renewal, migration, invasion, and anchorage independent cell growth. It is expected that nanoparticle delivery of specifically targeted RNA inhibitors will function as viable therapeutic approaches to aggressive neoplastic cancer. In addition, preliminary studies suggest that NP delivery of plasmid DNA expressing shRNA to target HMGA1 can be delivered to xenograft tumor cells and may impair growth.

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A method of treating an aggressive and/or poorly differentiated metastatic cancer in a subject in need thereof comprising administering a therapeutically effective amount of at least one HMGA1 inhibitor to the subject, wherein the aggressive and/or poorly differentiated metastatic cancer comprises at least one cancer stem cell that overexpresses HMA1 protein.

2. The method of claim 1, wherein the aggressive and/or poorly differentiated metastatic cancer is selected from the group consisting of triple-negative breast cancer, pancreatic ductal adenocarcinoma cell, colorectal cancer cell, and leukemia.

3. The method of claim 1, further comprising selecting the subject for treatment of the aggressive and/or poorly differentiated metastatic cancer with the at least one HMGA1 inhibitor.

4. The method of claim 3, wherein selecting the subject for treatment of the aggressive and/or poorly differentiated metastatic cancer comprises: (i) obtaining a biological sample comprising cells from the aggressive and/or poorly differentiated metastatic cancer; (ii) assaying the level of HMGA1 expression in the cells from the aggressive and/or poorly differentiated metastatic cancer; (iii) comparing the level of HMGA1 expression in the cells to the level of HMGA1 expression in a normal control cell; and (iv) selecting the subject for treatment of the aggressive and/or poorly differentiated metastatic cancer with the at least one HMGA1 inhibitor if the level of HMGA1 expression in the cells is greater than the level of HMGA1 expression in the normal control cell.

5. The method of claim 4, wherein the biological sample is selected from the group consisting of a breast tissue sample, a pancreatic tissue sample, a colon tissue sample, and a bone marrow tissue sample.

6. The method of claim 4, wherein at least some of the cells from the aggressive and/or poorly differentiated metastatic cancer comprise cancer stem cells.

7. The method of claim 1, wherein the at least one HMGA1 inhibitor reduces the expression level and/or activity of HMGA1.

8. The method of claim 1, wherein the at least one HMGA1 inhibitor is formulated for delivery in a nanoparticle.

9. The method of claim 1, wherein the at least one HMGA1 inhibitor is an RNA interfering agent.

10. The method of claim 9, wherein the at least one HMGA1 inhibitor is an shRNA.

11. The method of claim 10, wherein the shRNA targets the nucleotide sequence of SEQ ID NO:1.

12. The method of claim 10, wherein the shRNA is formulated for delivery in a nanoparticle.

13. The method of claim 1, wherein the subject is a human subject.

14. The method of claim 1, further comprising administering an effective amount of a chemotherapeutic agent to the subject.

15. The method of claim 14, wherein the chemotherapeutic agent is gemcitabine.

* * * * *

SEQUENCE LISTING

<160> NUMBER OF SEQ ID NOS: 1

<210> SEQ ID NO 1
<211> LENGTH: 21
<212> TYPE: DNA
<213> ORGANISM: Homo sapiens

<400> SEQUENCE: 1
caactccagg aaggaaacca a                                    21